United States Patent
Montgomery et al.

(10) Patent No.: US 6,457,984 B1
(45) Date of Patent: Oct. 1, 2002

(54) ELECTRICAL JACKBOX APPARATUS AND METHOD

(75) Inventors: Anthony R. Montgomery, Verona, WI (US); Peter Montgomery, Hornsby Heights (AU); Arthur A. Pratt, Madison, WI (US); Jeffrey P. Milsap, Cambridge, WI (US); Dan C. Strelow, Barneveld, WI (US); Ernest C. Jacobs, Vermont, WI (US)

(73) Assignee: La Mont, LLC, Madison, WI (US)

( * ) Notice: Subject to any disclaimer, the term of this patent is extended or adjusted under 35 U.S.C. 154(b) by 0 days.

(21) Appl. No.: 09/532,598

(22) Filed: Mar. 22, 2000

Related U.S. Application Data

(60) Provisional application No. 60/155,306, filed on Sep. 21, 1999.

(51) Int. Cl.[7] .............................................. H01R 13/44
(52) U.S. Cl. ........................ 439/131; 439/367; 439/460
(58) Field of Search ................................ 439/131, 367, 439/534, 607, 460, 465, 467, 470, 909, 488, 491

(56) References Cited

U.S. PATENT DOCUMENTS

| | | |
|---|---|---|
| 2,953,625 A | 9/1960 | Hasselhorn |
| 3,199,068 A | 8/1965 | Neenan |
| 3,601,746 A | 8/1971 | Teagno |
| 3,683,314 A | 8/1972 | Elkins |
| 3,904,936 A | 9/1975 | Hamrick, Jr. et al. |
| 4,103,985 A | 8/1978 | Krolak et al. |
| 4,372,629 A * | 2/1983 | Propst et al. ............... 439/131 |
| 4,382,649 A | 5/1983 | Meyer |
| 4,946,397 A | 8/1990 | Grässer |
| 4,986,762 A | 1/1991 | Keith |
| 5,231,562 A * | 7/1993 | Pierce et al. ................ 439/131 |
| 5,244,408 A | 9/1993 | Muller et al. |
| 5,370,553 A | 12/1994 | Zimmerman |
| 5,395,248 A | 3/1995 | Kinoshita et al. |
| 5,639,261 A | 6/1997 | Rutkowski et al. |
| 5,896,478 A | 4/1999 | Dauber et al. |
| 5,967,836 A | 10/1999 | Bailey |
| 5,984,720 A | 11/1999 | Milner et al. |
| 6,069,315 A * | 5/2000 | Tang .......................... 439/460 |
| 6,099,340 A * | 8/2000 | Florentine ................... 439/367 |

FOREIGN PATENT DOCUMENTS

JP 5-211085 8/1993

* cited by examiner

*Primary Examiner*—Tho D. Ta
(74) *Attorney, Agent, or Firm*—Michael Best & Friedrich LLP

(57) ABSTRACT

In the jackbox of the present invention, a number of electrical connectors are releasably connectable to electrical leads carrying electrical signals representative of at least one physiological patient parameter from the patient to patient monitoring equipment. Preferably, the jackbox has an openable enclosure for gaining access to electrical connectors therein. When closed, the enclosure preferably substantially surrounds the electrical connectors and ends of the electrical leads. The enclosure can have a clamshell, book, or other form as desired. Although an openable enclosure is preferred, some embodiments of the jackbox have no enclosure or have an enclosure not permitting user access to the interior thereof. Enclosures according to different embodiments of the present invention are made of resilient and relatively non-deformable, semi-deformable, or deformable material. To improve access to the electrical connectors, one or more of the electrical connectors are preferably movable in response to motion of the enclosure and/or are preferably arranged in a space-saving nested relationship. Electrical connector nesting can be between electrical connections substantially overlying one another or only partially overlapping one another. Highly preferred embodiments have electrical connectors arranged in sets of partially overlapping electrical connections. Also, each set is preferably offset with respect to the set or sets of electrical connectors located therebehind. Preferably, the electrical connectors are also arranged to prevent inadvertent or accidental disconnection of the electrical leads and to prevent the transmission of pulling force upon the electrical leads outside of the jackbox to the electrical connections inside the jackbox.

181 Claims, 9 Drawing Sheets

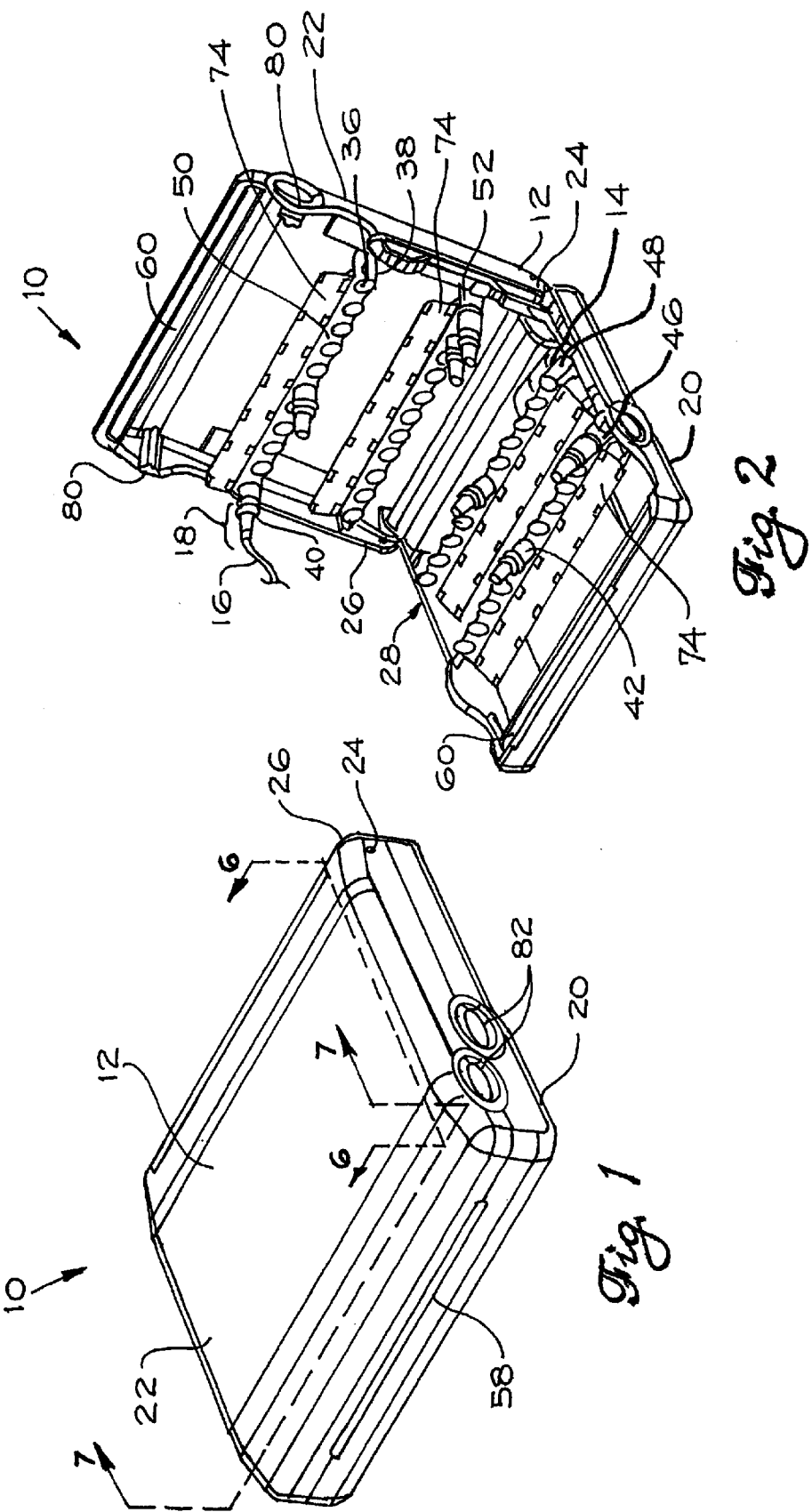

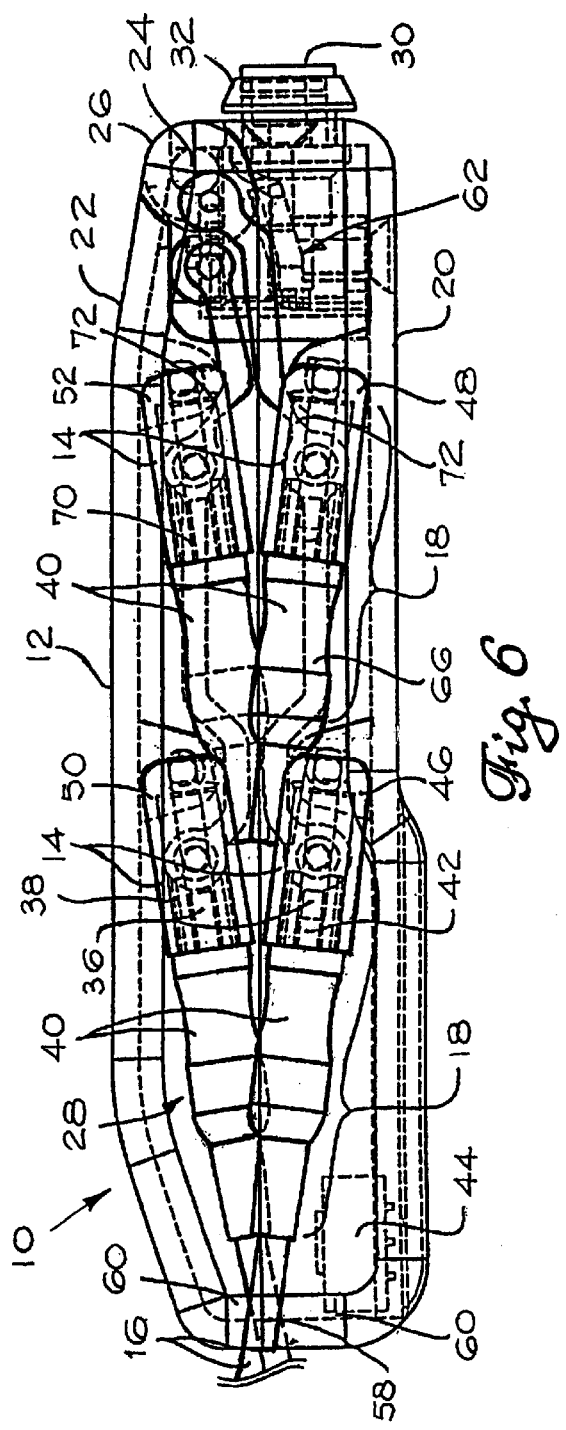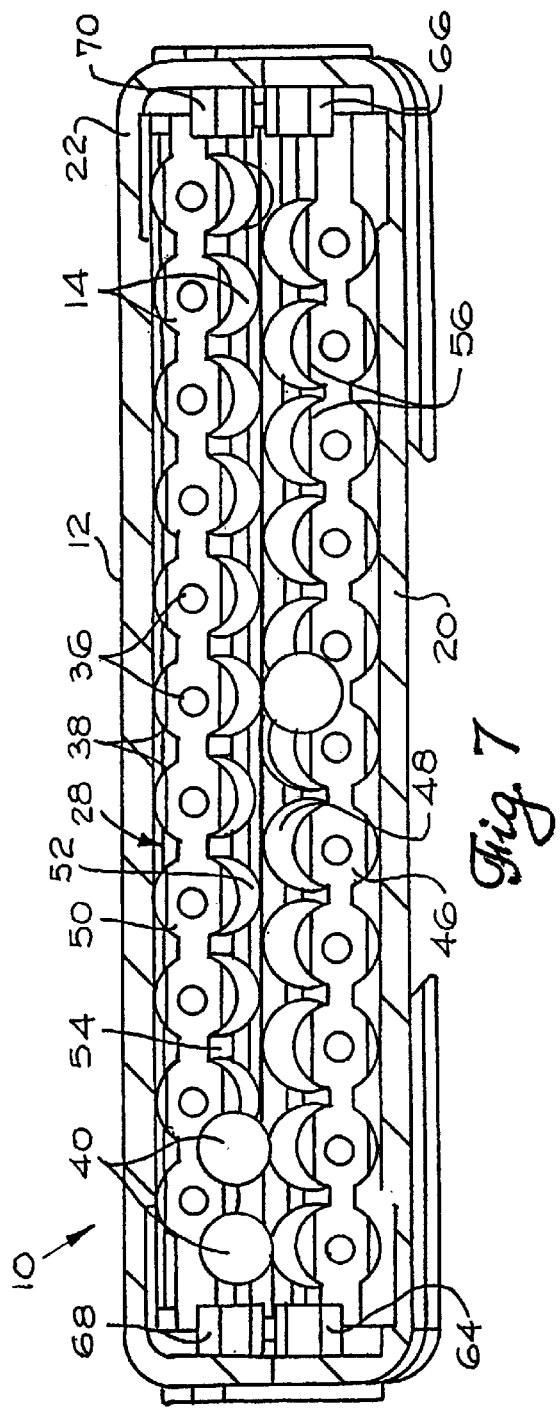

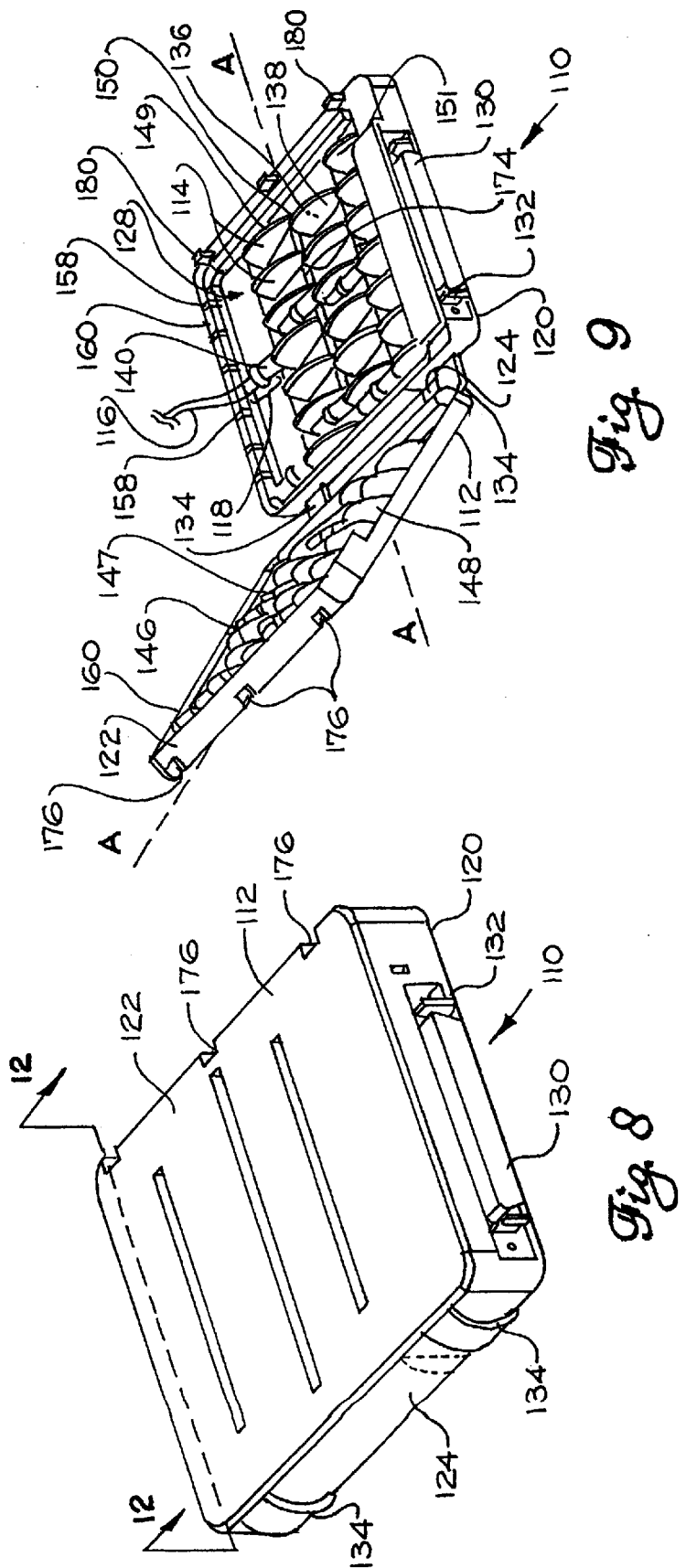

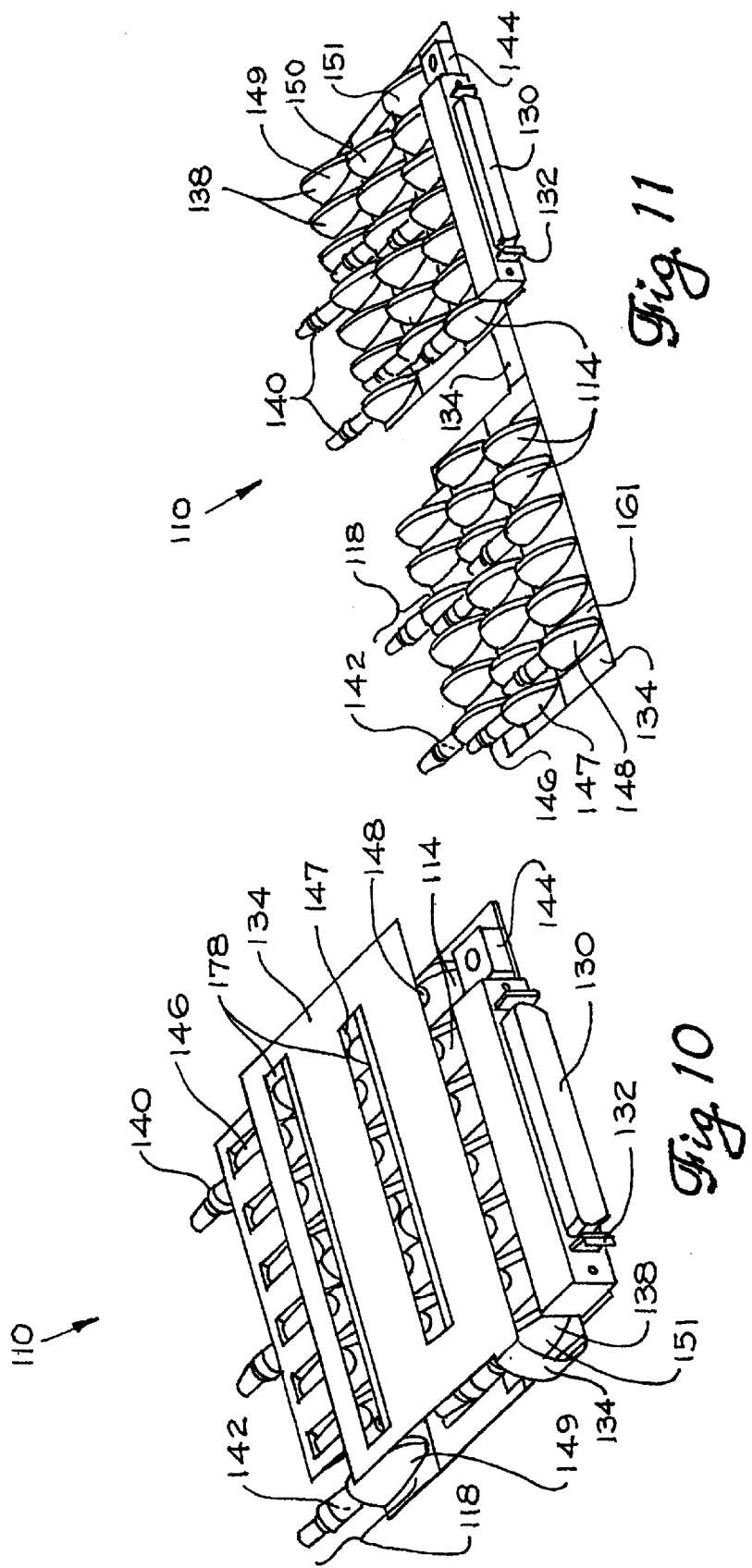

ELECTRICAL JACKBOX APPARATUS AND METHOD

Priority is claimed to U.S. patent application Ser. No. 60/155,306, which was filed on Sep. 21, 1999.

FIELD OF THE INVENTION

This invention relates generally to electrical connector housings and terminals, and more particularly to jackboxes for connecting electrical lines carrying electrical signals relating to physiological parameters.

BACKGROUND OF THE INVENTION

In recent years, numerous technological advancements have been achieved in the field of patient monitoring. For example, improvements in the process of patient brain wave monitoring continue to be made. Whether for long term monitoring of epilepsy patients, sleep monitoring, routine electroencephalograms (EEGs), or other monitoring, these advancements have improved the quality, accuracy, and speed of diagnoses. However, improvements in the form, size, and weight of the medical equipment used for patient monitoring leave much to be desired. For example, typical neurophysiological monitoring equipment includes a number of depth and/or surface electrodes for sensing electrical signals from the patient's brain and other physiological parameters of the patient, a number of corresponding electrode leads for carrying those signals from the patient, a jackbox, a signal amplifier for amplifying the signals, and a recording device (e.g., a computer) for recording, display, output and/or analysis of the signals. The jackbox acts as a routing box, thereby connecting patient electrophysiological signals via the electrode leads to the amplifier, and is typically a box-shaped device having a port for connection to the amplifier or amplification circuitry (typically by a cable or a connection port) and a series of other ports for connection to the individual electrode leads. In addition, mobile systems can include one or more batteries and related power equipment.

In light of the above-described patient monitoring system, it will be appreciated that a conventional patient monitoring system can include a large number of components, many of which are commonly quite bulky and heavy. Bulky and heavy system components increases system transport and setup, and compromises patient mobility in mobile patient monitoring systems.

Although the size and weight of many devices in patient monitoring systems have been reduced to make setup and transport easier and to facilitate patient mobility, the jackbox in such conventional systems typically remains poorly suited for patient comfort and ease of use. A typical conventional jackbox such as in a neurophysiology patient monitoring system is a box-shaped metal or hard plastic device having a series of externally-exposed sockets on one or more faces. The interior of the jackbox is not accessible to a user, and houses internal wiring connecting the sockets to an externally-exposed cable port or multiple jacks on the jackbox. The jackbox essentially collects all electrical signals and routes them to the cable port or jack(s) for output to the next device (e.g., a signal amplifier or amplification circuitry). The series of externally-exposed sockets on the jackbox receive plugs of the electrical leads running to the patient, while the externally-exposed cable port or jack receives a cable running to a signal amplifier or other signal processing equipment.

This widely used conventional jackbox design has a number of limitations. First, the conventional large and heavy jackboxes are undesirable because they occupy valuable space in patient quarters, increase patient discomfort in applications where the jackbox is worn, and are generally more difficult to transport even if not worn by the patient. Because these factors make conventional jackboxes (and indeed, the entire patient monitoring system) less desirable from a patient's point of view, they can affect the patient's desire to use the system. Especially in more difficult applications such as for longer-term monitoring or where the patient is an infant, child, or is mentally ill, these factors can even determine whether a particular patient monitoring system can be reliably used.

Also, conventional patient monitoring system jackboxes are not well suited to be worn by a patient. The size, weight, design, and hard material of such jackboxes makes them uncomfortable for a patient to wear.

The ability of electrodes to become disconnected from the jackbox readily presents another problem for conventional patient monitoring jackboxes. Because the electrode leads from the patient's body typically run to externally exposed electrical connections (e.g., sockets or pins) on the jackbox (which typically provides no strain relief for the leads or connections), the chances of accidental disconnection at the patient or on the jackbox connection points are significant—especially for mobile or long-term monitoring systems or where the patient is otherwise fairly active. Reliable and accurate monitoring is mission critical because the results of the monitoring can be used to determine the need for and extent of surgery. Accordingly, disconnection of patient electrode leads may ruin monitoring results and require additional subsequent monitoring. Although special connectors can be used to secure the electrode leads to the jackbox (such as screw mounts or side clips for each lead), these connections are often difficult to manipulate, especially for typical applications where a bundle of 30 or more leads must be connected to the jackbox and only a limited number break or disconnect.

As described above, conventional jackboxes typically have external connectors. This exposes the jackbox and lead connections to contaminants such as dirt, dust, and spilled liquid, and increases the possibility of connection corrosion. Such externally exposed connections are also more likely to be bent, broken, or otherwise damaged, thereby resulting in missed, loose or poor connections that may not be detected by the user.

Yet another problem common to most conventional jackboxes relates to the large number of electrode leads typically connected to the jackbox. Many applications call for over 30 electrode leads to be connected. Conventional jackbox designs themselves do not provide any manner or structure by which the electrode leads can be organized and prevented from tangling. Also, because the leads are often connected in relatively tight, ganged, or gathered sets on the exterior of the jackbox, the process of connecting, disconnecting, and changing electrode leads on the jackbox can be difficult. For example, each electrode lead is typically assigned a specific connector on the jackbox. When sets of several connectors are to be connected to corresponding electrode leads, lack of organization can cause switched and improper connections that can generate incorrect monitoring results that may not be detected by the user.

The practice of tightly bundling the connectors on a conventional jackbox can serve the purpose of reducing jackbox size, but at the cost of making jackbox connection and setup difficult. This practice, along with the lack of lead organization in conventional jackboxes, can significantly increase the time needed to set up a patient monitoring system. Attempts continue to be made in such jackbox designs to label the jackbox connectors for making setup easier and more reliable, but only with limited success. The ability to provide large and clear labels or other indicia for closely grouped jackbox connectors and electrode leads remains a problem.

In addition to the problems discussed above with regard to external electrical connections, conventional jackboxes employing such connections are also exposed to electromagnetic interference. Such interference may detrimentally affect monitoring results.

In light of the problems and limitations of the prior art described above, a need exists for an apparatus and method for connecting a plurality of patient monitoring electrodes to associated equipment in which the device used for such connections is small, lightweight, resistant to damage, and comfortable to wear, which provides releasable electrode lead connections that are reliable and are protected from electromagnetic interference, accidental disconnection, damage due to forces exerted upon the electrode leads, corrosion, and contaminants such as dirt, dust, fluids, and the like, and which enables quick, easy, and accurate connection of the electrode leads to corresponding connectors. Each preferred embodiment of the present invention achieves one or more of these results.

SUMMARY OF THE INVENTION

The present invention is a jackbox for releasable connection of a plurality of electrical leads carrying electrical signals representative of at least one physiological patient parameter to patient monitoring equipment. The jackbox has a number of electrical connectors which are releasably connectable to the electrical leads. Preferably, the jackbox has an enclosure that can be opened and closed to gain access to electrical connectors therein and which offers protection of the leads and connection points of such. When closed, the enclosure preferably substantially surrounds the electrical connectors and ends of the electrical leads connected thereto. Unlike conventional jackboxes for patient monitoring systems, such enclosures provide protection for electrical connectors and electrical leads against dirt, dust, spilled liquids, electrical connector or lead corrosion, potentially damaging pulling, pushing, and bending forces, and other damage from environmental exposure. Also, such enclosures permit shielding material to be used to shield the electrical connectors and electrical leads from electromagnetic interference.

Some preferred embodiments of the present invention employ a clamshell-style enclosure, others employ a book-shaped enclosure, while still others have enclosures shaped and openable in any desired manner. Although a jackbox having an openable and closable enclosure is preferred, other embodiments of the jackbox have no enclosure or have an enclosure that does not permit user access to the interior thereof.

Enclosures according to different embodiments of the present invention are made of resilient material that is relatively non-deformable, semi-deformable, or deformable for serving a number of different purposes. Jackbox embodiments having a resilient and relatively non-deformable enclosure can be used for providing more jackbox strength and a more rigid jackbox structure (useful, for example, where electrical connector pivot mechanisms are desired or where certain types of electrical connector movement are desired as described below). Jackbox embodiments having a resilient and semi-deformable or deformable enclosure can be used for providing increased wearer comfort, increased protection against dropping, impact or other shock, and where certain other types of electrical connector movement are desired as also described below.

To improve access to the electrical connectors in the jackboxes of the present invention, one or more (and most preferably all) of the electrical connectors are preferably movable. In one preferred embodiment for example, the electrical connectors are connected to a pivot mechanism that is coupled to the jackbox enclosure. When the enclosure is opened or closed, such enclosure motion causes motion of the pivot mechanism which in turn causes motion of the electrical connectors. The pivot mechanism in highly preferred embodiments of the present invention is a series of elongated linking elements coupled to the enclosure and to the electrical connectors for motion transfer from the enclosure to the electrical connectors. Most preferably, the linking elements are pivotably mounted to the enclosure and to the electrical connectors arranged singularly or in groups or "sets". Other embodiments of the present invention transfer enclosure motion via linking elements to rotational, translational, or both rotational and translational motion of the electrical connectors. In each case, the electrical connectors are moved between a position in which they are preferably in a compact and space saving storage arrangement and a position in which they are preferably in a more spaced apart arrangement for increased user access. In one highly preferred embodiment, linking elements are pivotably coupled to the electrical connectors and cause the electrical connectors to pivot about pivot points on the enclosure when the enclosure is opened or closed. In the closed position, the electrical connectors are preferably all close together and oriented in the same general direction while in the open position, the electrical connectors are rotated to space apart the electrical connectors and to "fan" or spread apart the electrical leads connected thereto for increased user access. Spaced or fanned electrical connections and electrical leads are easier to identify, label, connect and disconnect, reduce the chances of incorrect connections and setup error, and accelerate the jackbox connection process.

In another preferred embodiment of the present invention, improved electrical connector access is enabled by employing a resilient and semi-deformable or deformable jackbox enclosure design. Specifically, one or more portions of the enclosure can be bent, twisted, or otherwise deformed by the user to better expose the electrical connectors inside. With such manipulation, the electrical connectors can be moved with the deformed material into a fanned or spread orientation from a relatively close and space-saving arrangement, resulting in the same advantages as described above.

Regardless of enclosure material, shape, or manner of opening, the electrical connectors are preferably arranged in a space-saving relationship at least when the jackbox is in a closed position. As described above, this can be accomplished by moving the electrical connectors as the jackbox is closed. This can instead or also be accomplished by employing preferred electrical connector arrangements and orientations within the closed jackbox. In highly preferred embodiments of the present invention, the electrical connectors are nested within one another, whether in bundled sets, in layered rows, etc. Such nesting can be between sets of electrical connections (defined as electrical connectors coupled to electrical leads) coupled directly or indirectly to the same enclosure portion of the jackbox or can be between sets of electrical connections coupled directly or indirectly to different enclosure portions of the jackbox (such as to two portions movable with respect to one another to open and close the jackbox). Most preferably however, electrical connections are nested not only on the same enclosure portions but also between different enclosure portions of the jackbox.

Electrical connector nesting in the present invention can be between electrical connections substantially overlying one another or only partially overlapping one another. In a partially overlapping relationship, the electrical connectors of one set of electrical connections are nested within the electrical connectors and/or the electrical leads of one or more other sets of electrical connectors. Highly preferred embodiments of the present invention have electrical connectors arranged in sets of partially overlapping electrical connectors. Also, each set of electrical connectors is preferably offset with respect to the set or sets of electrical connectors located therebehind. Offset electrical connector sets are preferable because they facilitate electrical connection nesting (described above) and because they provide improved centrally-gathered feed paths for electrical leads running out of the jackbox thereby helping reduce strain on the electrical connections.

By conserving space in the jackbox through movement of the electrical connectors into a compact storage position when the jackbox is closed and by employing a nested arrangement of electrical connections in the jackbox, the present invention provides a jackbox of significantly reduced size that is less obtrusive and that is easier and more comfortable to wear.

Preferably, the electrical connectors in the present invention are arranged to prevent inadvertent or accidental disconnection of the electrical leads from the electrical connectors and to prevent the transmission of pulling force upon the electrical leads outside of the jackbox to the electrical connections inside the jackbox. To this end, the electrical connectors are preferably arranged in the jackbox so that each set of electrical connections (i.e., electrical leads and/or electrical connectors) blocks the removal of the electrical leads behind them. In highly preferred embodiments of the present invention, this blocking is the result of the nested electrical connection relationship described above, but does not require nesting to be effective. Those electrical connections having no electrical connections in front of them are preferably blocked from removal by one or more retaining elements preferably attached to or integral with the enclosure. In other embodiments of the present invention, one or more retaining elements are located in front of and block disconnection of any number of electrical connectors located anywhere in the jackbox. Preferably, the retaining elements hold the electrical leads and prevent the transmission of pulling force from outside of the jackbox to the leads inside the jackbox.

Some preferred embodiments of the present invention can employ wireless transmitters and receivers for transmitting signals from the jackbox to downstream equipment. Jackboxes employing this feature preferably have an amplifier, digitizer, and transmitter (or signal amplification, digitization, and transmission circuitry) for processing and transmitting the signals to such downstream equipment. Although such jackboxes preferably have an amplifier, digitizer, and transmitter connected to or part of the jackbox circuitry, an external amplifier, digitizer, and transmitter can also be used if desired. Alternative embodiments of the wireless jackbox can employ different arrangements of these components, such as a digitizer connected to the receiver of downstream equipment rather than on or connected to the jackbox, a jackbox having an amplifier upstream of the digitizer rather than a digitizer upstream of an amplifier, and the like. In still other embodiments of the present invention, the electrical leads running from the patient's body to the jackbox can be replaced by a series of amplifiers, digitizers, and wireless transmitters each connected to a respective sensor on the patient and capable of transmitting signals to one or more receivers in, on, or connected to the jackbox and/or other receiving devices (such as a computer).

Further objects and advantages of the present invention, together with the organization and manner of operation thereof, will become apparent from the following detailed description of the invention when taken in conjunction with the accompanying drawings, wherein like elements have like numerals throughout the drawings.

BRIEF DESCRIPTION OF THE DRAWINGS

The present invention is further described with reference to the accompanying drawings, which show a preferred embodiment of the present invention. However, it should be noted that the invention as disclosed in the accompanying drawings is illustrated by way of example only. The various elements and combinations of elements described below and illustrated in the drawings can be arranged and organized differently to result in embodiments which are still within the spirit and scope of the present invention.

In the drawings, wherein like reference numerals indicate like parts:

FIG. 1 is a front perspective view of the jackbox according to a first preferred embodiment of the present invention, showing the jackbox in its closed position;

FIG. 2 is a front perspective view of the jackbox illustrated in FIG. 1, showing the jackbox in an open position;

FIG. 6 is a side cross-sectioned elevational view of the jackbox illustrated in FIGS. 1–5 taken along lines 6—6 in FIG. 1;

FIG. 7 is a front elevational view of the jackbox illustrated in FIGS. 1–6, taken along lines 7—7 in FIG. 1;

FIG. 8 is a front perspective view of the jackbox according to a second preferred embodiment of the present invention, showing the jackbox in its closed position;

FIG. 9 is a front perspective view of the jackbox illustrated in FIG. 8, showing the jackbox in an open position;

FIG. 10 is a front perspective view of the jackbox illustrated in FIGS. 8 and 9, showing the jackbox in its closed position with the enclosure material removed;

FIG. 11 is a front perspective view of the jackbox illustrated in FIGS. 8–10, showing the jackbox in an open position with the enclosure material removed;

DETAILED DESCRIPTION OF THE PREFERRED EMBODIMENTS

Figure 4:
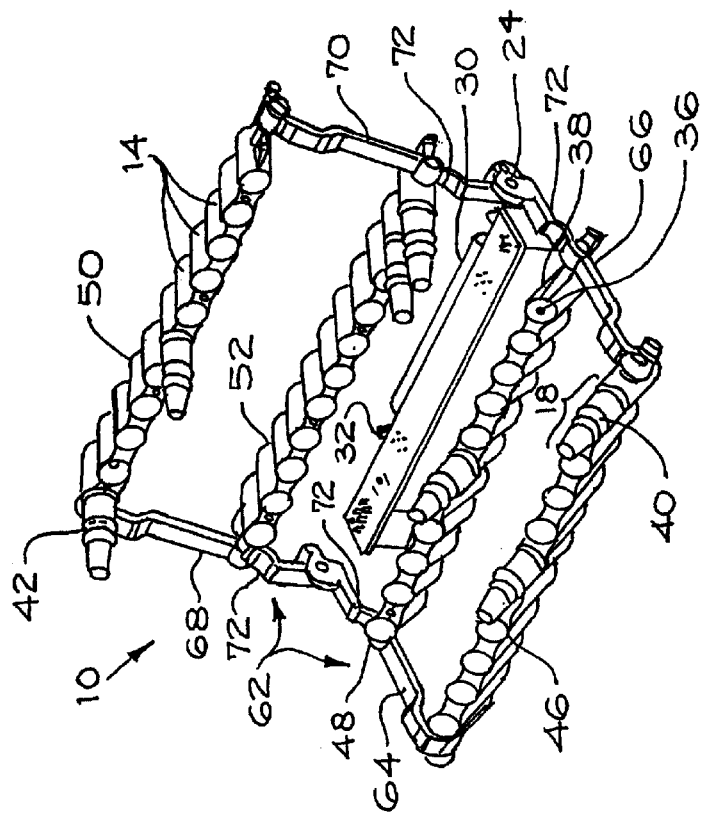
FIG. 4 is a front perspective view of the jackbox illustrated in FIGS. 1–3, showing the jackbox in an open position with the enclosure removed.

The jackbox of the present invention provides a series of electrical connectors to which the plurality of electrode leads can be releasably connected in an organized manner to downstream equipment such as one or more signal processors, amplifiers or amplification circuitry, and the like. Two preferred embodiments of the present invention are shown by way of example in FIGS. 1–7 and 8–12, respectively.

With reference first to the embodiment of FIGS. 1–7, the jackbox 10 preferably has an enclosure 12 within which are mounted a number of electrical connectors 14 for releasable connection to a number of electrical leads 16 (the ends of a few being shown in the figures). The electrical connectors 14 are mounted within the jackbox 10 by being directly or indirectly connected (e.g., attached, formed, or otherwise coupled) to the enclosure 12 and/or by being connected to framework or other structural elements of the jackbox 10 as will be described in more detail below. The enclosure 10 is preferably made of lightweight plastic, but can instead be made of any resilient material desired, including without limitation aluminum, steel, and other metals, urethane, composites, ceramics, and the like. Many such materials are compatible with conventional sterilization procedures such as, for example, gas autoclave sterilization, allowing the enclosure 12 to be used in sterile medical procedures (such as a surgical procedure in an operating room). It should be noted that the other elements in the jackbox 10 of the present invention (described below) are preferably made from such materials. The ability to sterilize the jackbox 10 and its components is particularly valuable because it permits use of the jackbox 10 in sterile medical procedures where -the jackbox 10 is located close to the patient within the sterile field of the operation.

The enclosure 10 can take a number of different shapes, such as a rectangular, square, round, oval, polygonal, or irregularly-shaped box having faceted, blunted, radiused, or even sharp corners and edges. In this preferred embodiment, however, the enclosure is a relatively flat and square box with rounded edges and corners as best shown in FIG. 1. The square shape is preferred based upon the preferred arrangement of internal electrical connectors and leads as will be described in more detail below. Other relatively flat shapes are also preferred based upon alternative numbers and arrangements of these elements. Relatively flat enclosures are preferred due to their advantages of being compact and wearable close to a patient's body. Of course, where patient mobility is less of a concern, still other enclosure shapes can instead be used.

The preferred jackbox embodiment shown in FIGS. 1–7 employs a clamshell-type enclosure to enclose the electrical connections therein (each electrical connection 18 being defined by an electrical connector 14 and an end of the electrical lead 16 connected thereto). In the present description and in the appended claims, the term "clamshell" refers to a structure having two primary body parts hinged or otherwise movable with respect to one another with the hinge or other coupler running substantially horizontally at the rear of the structure when opened and facing the user. Most preferably, the two primary body parts are hinged at respective adjacent rear edges as shown in the figures. However, in less preferred embodiments of the clamshell enclosure, the hinge can be located at a rear edge of one primary body part and forward of the rear edge of the other primary body part.

The clamshell enclosure of the preferred jackbox embodiment shown in FIGS. 1–7 has a base 20 and lid 22 hinged for relative movement at hinge 24. The hinge 24 can take any conventional form, such as an elongated post extending through apertures at the rear of the base 20 and lid 22, two or more pins passed through adjacent pairs of flanges on the rear of the base 20 and lid 22, one or more portions of flexible material such as plastic, fabric, and the like attached to or integral with the base 20 and lid 22, etc. In the illustrated preferred embodiment, flanges 26 of the lid 22 are hinged to the rear of the base 20 by hinge pins (not shown). Most preferably, the hinge mechanism (i.e., pins, integral mating portions, and the like) is internal to the enclosure 12, as is the case with the illustrated preferred embodiments of the present invention. Where pins, posts, or other hinge elements are exposed to the exterior of the enclosure, these elements are preferably rounded, chamfered, and/or recessed. These feature makes the jackbox 10 more comfortable to wear and less susceptible to being caught on clothing and nearby articles.

When pivoted to the closed position shown in FIG. 1, the base 22 and lid 24 of the enclosure 10 define a chamber 28 therebetween. The chamber 28 preferably substantially encloses the electrical connections 18 when the enclosure 10 is closed.

The jackbox 10 operates to establish electrical communication (or wireless communication as described below) between the electrical leads 16 and a device electrically coupled to the jackbox. The jackbox 10 and device can be electrically coupled in any number of manners well known to those skilled in the art. For example, the jackbox 10 can have one or more electrical ports (in electrical communication with the electrical connectors 14 and electrical leads 16) for connecting one or more cables thereto or for connection directly to an electrical port of the device in a conventional manner, can have a transmitter for transmitting signals representative of the electrical signals received from the electrical leads 16, and the like.

Figure 3:
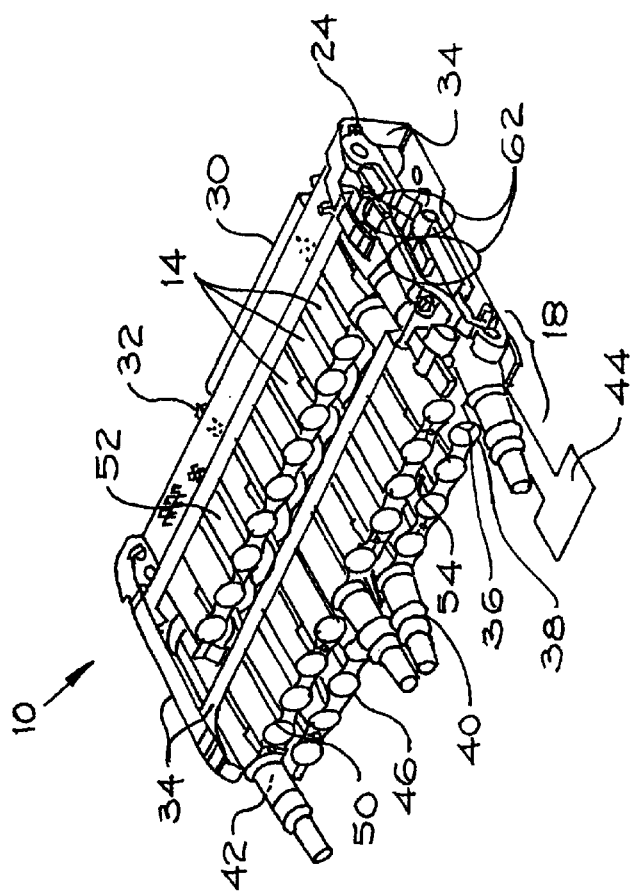
FIG. 3 is a front perspective view of the jackbox illustrated in FIGS. 1 and 2, showing the jackbox in its closed position with the enclosure removed.
Figure 5:
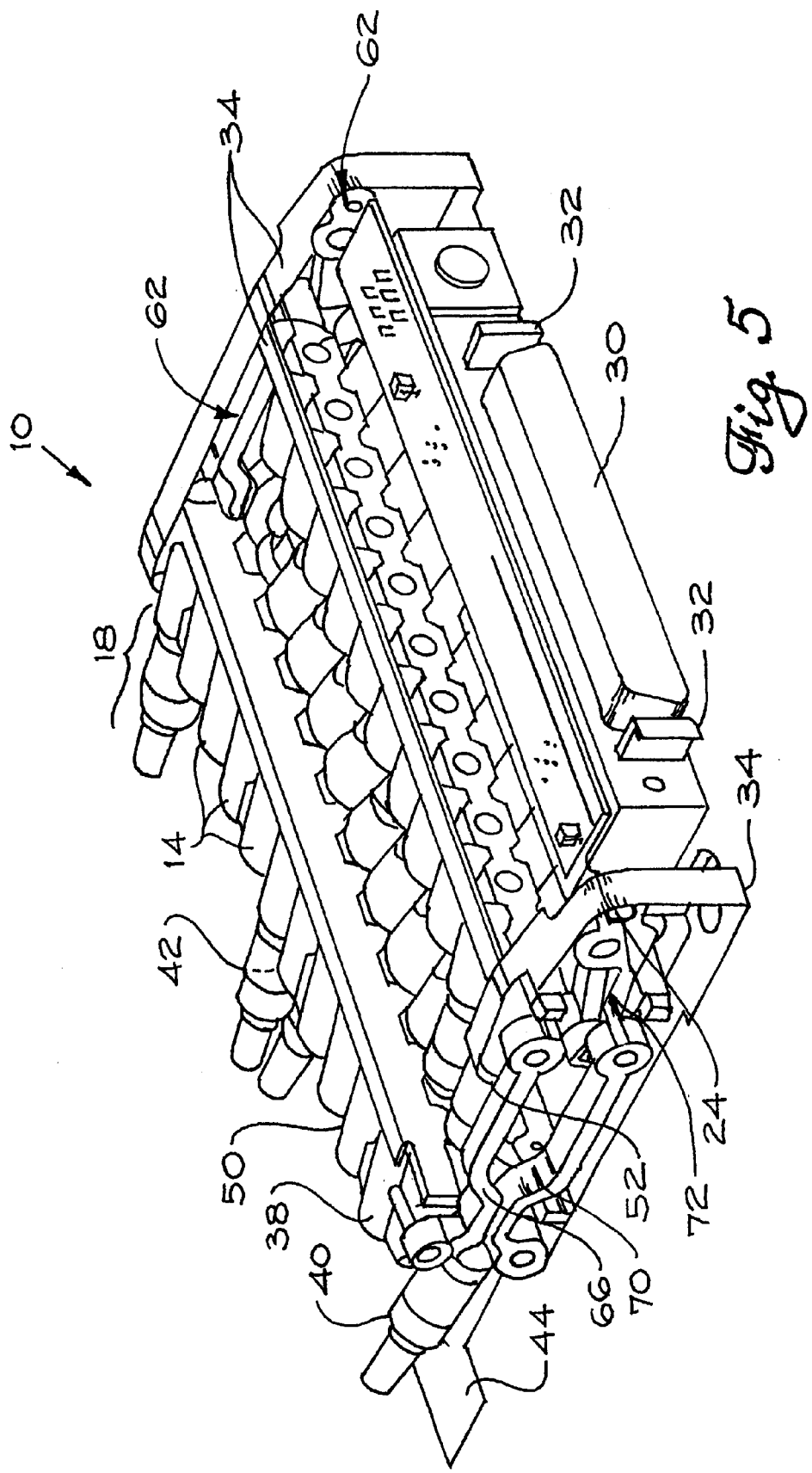
FIG. 5 is a rear perspective view of the jackbox illustrated in FIGS. 1–4, shown with the enclosure removed.
Figure 12:
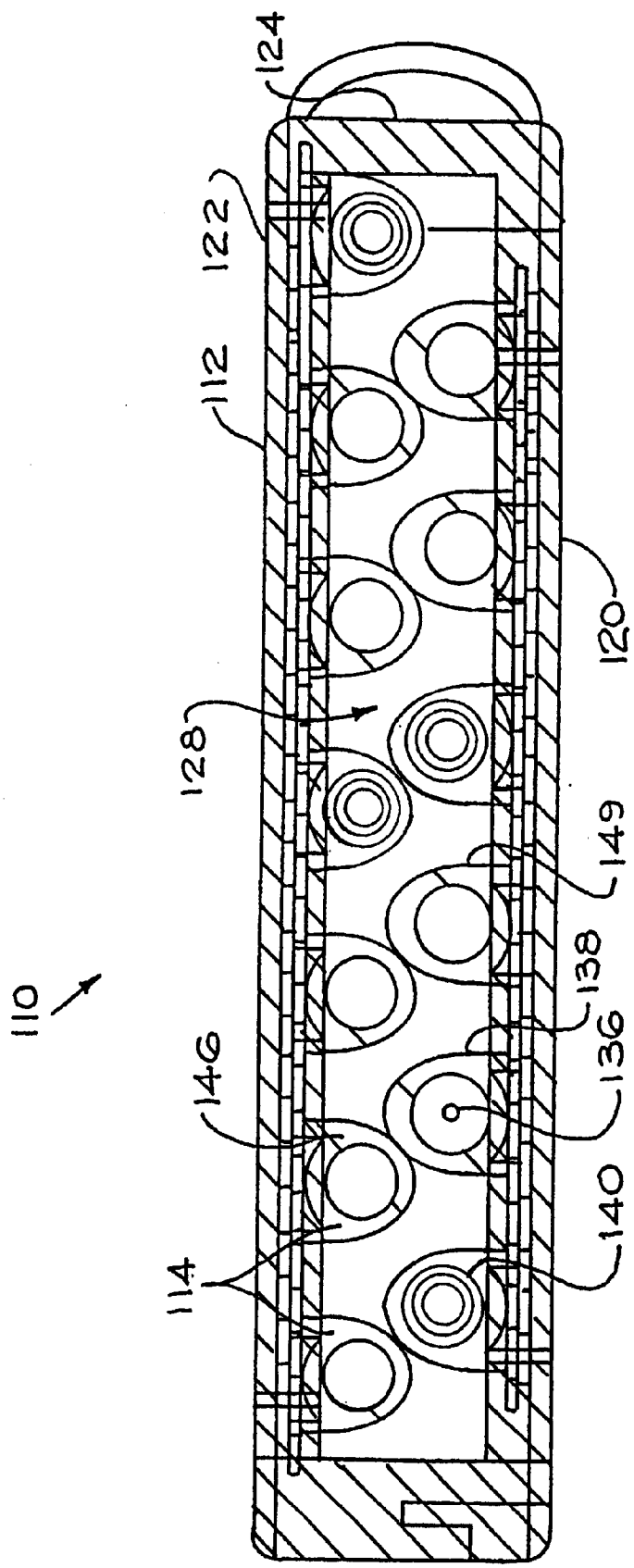
FIG. 12 is a front cross-sectioned elevational view of the jackbox illustrated in FIGS. 8–11, taken along lines 12—12 in FIG. 8.

The preferred embodiment illustrated in FIGS. 1–7 has an electrical port 30 mounted to the enclosure 10 for connection to a signal amplifier either directly or via a conventional cable. Standard port clips 32, thumbscrews, or like elements can be used to secure the connection to the electrical port 30. To transmit signals received from the electrical leads 16 to the electrical port 30 in this embodiment, the jackbox 10 has circuitry extending from each electrical connector 14 to the electrical port 30. This circuitry can take any form well known to those skilled in the art, but most preferably is one or more conventional flex circuits 34. The flex circuits 34 are preferably in thin and flat form as is best shown in FIGS. 3–5, permitting the circuits to run between electrical connectors 14 or between sets of electrical connectors 14 that are not necessarily aligned or are located in different positions within the chamber 28. However, one having ordinary skill in the art will appreciate that any type of electrical circuitry can be used to electrically connect the port 30 to the electrical connectors 14, including without limitation circuit boards to which the electrical connectors 14 and port 30 are mounted, wire tape, or even bundled wire leads or wireless transmitters. The preferred flex circuits 34 can be electrically connected to each of the electrical connectors 14 and to the electrical port 30 in any conventional fashion, but preferably are connected by soldering.

Figure 14:
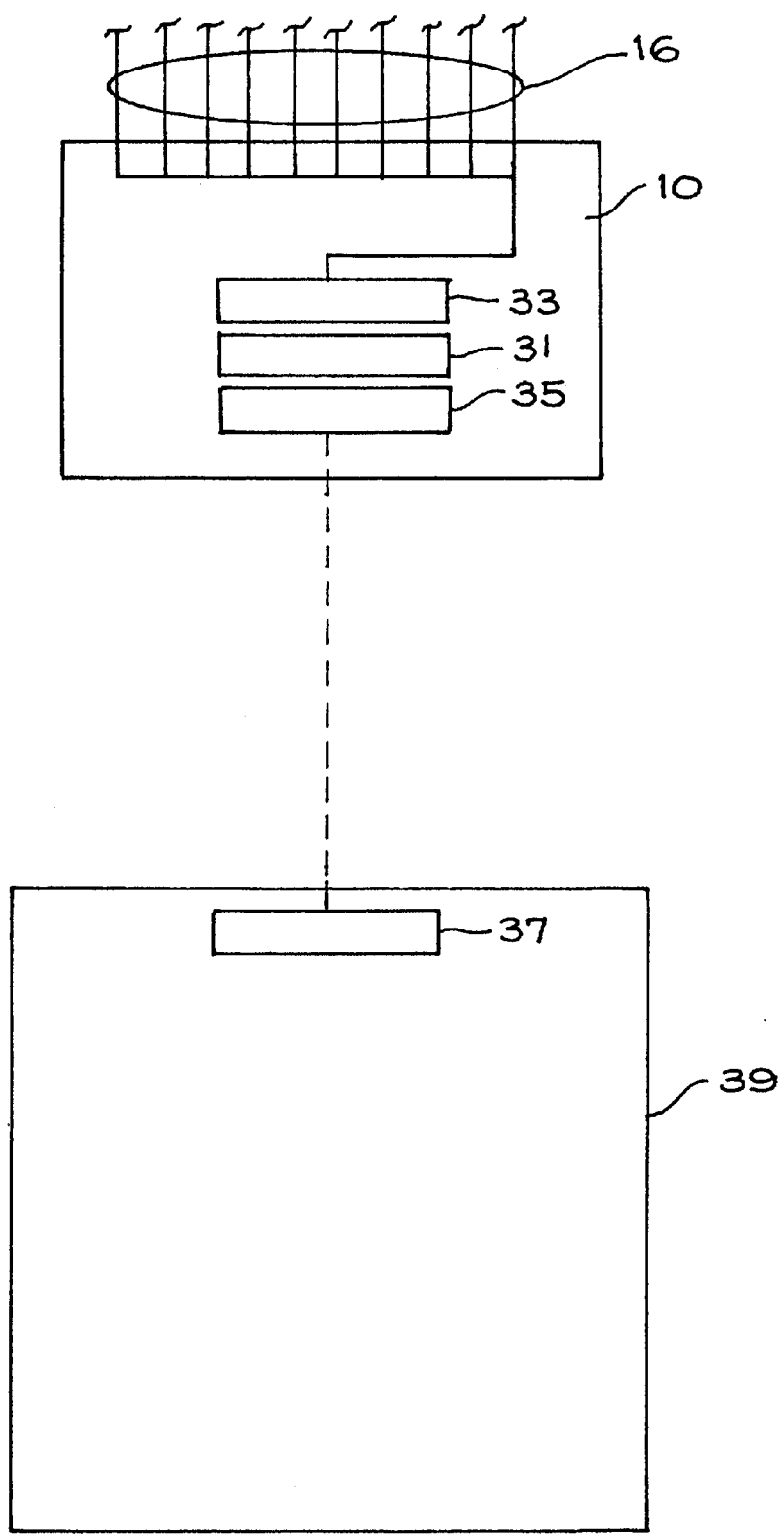
FIG. 14 is a schematic diagram of a wireless jackbox according to a preferred embodiment of the present invention.

As an alternative to jackboxes that are physically electrically connected to transmit signals to a receiving device, the jackbox 10 can be adapted for wireless transmission of signals received from the electrical leads 16 as shown in flowchart form in FIG. 14. Specifically, the jackbox can have a wireless transmitter in place of or in addition to the electrical port 30 described above. Conventional flex circuits (or other circuitry described above with reference to the jackbox shown in FIGS. 1–7) preferably transmit signals from the electrical connectors 14 to conventional digitization circuitry (digitizer 31 in FIG. 14), which converts the amplified analog signals from the electrical leads 16 to digital signals in a manner well known to those skilled in the art. The wireless transmitter employed can be selected from one of a number of different possible transmitters operating at any frequency, including without limitation optical (e.g., infrared, ultraviolet, etc.), radio, microwave, spread spectrum, and other frequencies. The digitizer 31 is preferably connected to or includes an amplifier 33 which receives and amplifies the acquired signals. The amplified digital signals are then transmitted by a conventional transmitter 35, which is on or more preferably in the jackbox 10. These signals are received by a conventional receiver 37 connected to downstream equipment, such as a recording device or computer 39.

Although signals from the jackbox 10 can be transmitted to a receiver as just described, one having ordinary skill in the art will appreciate that a number of other component arrangements can be employed to the same effect of transmitting electrical signals from the jackbox to a receiver. For example, the signals received from the electrical leads 16 need not necessarily be digitized as described above. Signals from the electrical leads 16 can instead be transmitted to the receiver and can be digitized or otherwise processed thereafter in a number of different manners well known to those skilled in the art. The jackbox 10 therefore need not have a digitizer or digitization circuitry. Also, the jackbox 10 need not necessarily have an amplifier 33 or amplification circuitry as described above, and can instead rely upon signal amplification by an amplifier connected to the jackbox 10 in any conventional manner. Although the transmitter 35 is preferably located on (and more preferably in) the jackbox 10, it should be noted that the transmitter 35 can also be separate from the jackbox 10 and connected thereto in any conventional manner, such as a separate transmitter 35 that is part of or connected to an amplifier connected to the jackbox 10. Most preferably, however, a jackbox 10 employing wireless transmission of signals to a receiver has an amplifier, digitizer, and transmitter thereon or (more preferably) therein.

One having ordinary skill in the art will appreciate that the order in which the amplifier 33, digitizer 31, and transmitter 35 are shown in FIG. 14 can be changed if desired. For example, the digitizer 31 can be moved downstream of the receiver 37 as described above. Such alternative arrangements fall within the spirit and scope of the present invention. Also, any one or more of these components can be integral or otherwise part of the jackbox circuitry (e.g., part of flex circuits connected to the electrical connectors 14, part of a circuit board connected to the electrical connectors 14, and the like), or can be discreet components (e.g., chips, circuit boards, and the like) connected to the jackbox circuitry in any conventional manner. Amplifiers, digitizers, transmitters, and electronic circuitry performing signal amplification, digitization, and wireless transmission are well known to those skilled in the art and are not therefore described further herein.

Although the preferred embodiments of the present invention described herein and shown in the appended claims employ conventional electrical leads 16 running from a patient's body to the jackbox 10, it should be noted that the electrical leads 16 can be replaced by individual amplifiers and wireless transmitters connected to the sensors attached to the patient's body. These wireless transmitters can receive low-energy signals for transmission to a conventional receiver in the jackbox 10, where the signals can be transmitted wirelessly or otherwise to downstream equipment as described above. The transmitters can be powered in any conventional manner (e.g., batteries, energy-transmitting radio waves, and the like). In these alternative embodiments of the present invention, the electrical connectors 14 of the preferred embodiments would be replaced by one or more conventional receivers adapted to receive signals from the sensors attached to the patient's body.

The electrical connectors 14 and the ends of the electrical leads 16 are preferably connected via a male-female connection. In the illustrated preferred embodiment, the electrical connectors 14 each have a center pin 36 about which preferably is located a shroud 38, while the ends 40 of the electrical leads 16 each preferably have a socket 42 sized to snugly fit the pin 36. Preferably (and as is common in the art), the socketed ends 40 of the electrical leads 16 are enlarged to facilitate user handling and manipulation. One having ordinary skill in the art will appreciate that as an alternative to the above-described electrical connector and lead relationship, the ends of the electrical leads 40 can each have a pin (shrouded or unshrouded) sized to snugly fit sockets of the electrical connectors 14. Also, other electrical connector types can be used in place of the preferred electrical connectors 14 and electrical lead ends 18 described above and illustrated in the figures, and are well known to those skilled in the art. These alternative electrical connections therefore fall within the spirit and scope of the present invention.

The electrical connectors 14 can take almost any desired shape (having a square, round, oval or other cross section, elongated or short, etc.). For reasons that will be explained below, the electrical connectors 14 are preferably arranged in sets of attached or integral electrical connectors 14. It should be noted, however, that one, more, or all of the electrical connectors 14 can be separate from the others and take any exterior shape desired or convenient for mounting the connector(s) 14 in the enclosure 12.

Depending upon the manner of connection of the electrical connectors 14 to the electrical leads 16, the electrical connectors 14 can be made of virtually any resilient material. For example, in the preferred embodiment of the present invention as described above, each electrical connector 14 has a pin 36 within a shroud 38. In such a case, the shroud 38 is preferably made of electrically insulative material such as plastic, composites, ceramics, and the like. However, especially where each electrical connector 14 is otherwise electrically insulated from the other electrical connectors 14, the electrical connectors 14 can be made of thermally conductive material such as steel or other metals.

It may be desirable to secure the flex circuits 34 to some or all of the electrical connectors 14 in order to provide a more stable and secure connection between the flex circuit 34 and electrical connectors 14. Although the flex circuits 34 are preferably connected to the electrical connectors by the soldered connections to the pins 36, additional attachment of the flex circuits 34 helps to protect these electrical connections. The flex circuits 34 can be attached to each electrical connector 14 individually or in a number of locations in any well known manner, such as by conventional fasteners, adhesive, cohesive, snap-fitting or sliding into slots or tabs in the electrical connectors 14, or even by being molded to the electrical connectors 14. Most preferably however, adhesive is used to secure the flex circuits 34 to the electrical connectors 14. For purposes of aesthetics, the flex circuits 34 are preferably secured to the electrical connectors 14 in locations hidden from view by a user when the enclosure 12 is opened. For example, in the preferred embodiment of the present invention shown in the figures, the flex circuits 34 are attached to the rear portions of each of the electrical connectors 14 and run to the sides of the enclosure 12 as best shown in FIG. 5.

The jackbox 10 can also be provided with a jackbox identifier 44 for distinguishing the jackbox 10 from others used in the same patient monitoring system. Specifically, the various jackbox embodiments of the present invention can be used in connection with other jackboxes, whether of the present invention or otherwise. This can be helpful in applications where the number of desired electrodes exceeds the connection capacity of a given jackbox. In such a case, two or more jackboxes can be connected to associated equipment or can transmit information thereto in any conventional manner. The jackbox identifier 44 in each jackbox is used to distinguish each jackbox connected to a patient. The jackbox identifier 44 could additionally/alternatively be used to distinguish between jackboxes connected to two or more different patients who are being monitored simultaneously by a single monitoring system. The jackbox identifier 44 can take any form well known to those skilled in the art, but preferably includes at least one multi-pole pin or a series of dual-position pins or switches that are user adjustable to different settings for assigning the jackbox 10 one of a number of unique identities. The jackbox identifier 44 can be referenced (e.g., by a connected recording device) via one or more of the flex circuits 34.

The jackbox 10 can also be provided with a power switch (not shown) electrically connected in a conventional manner to one or more of the flex circuits 34 and preferably mounted to the enclosure 12 in a conventional manner. The power switch can be used to control power to any part of the patient monitoring system as desired.

Preferably, at least one of the electrical connectors 14 is a reference electrical connector for connection to an electrical lead 16 transmitting reference signal(s) from the patient. The use of a reference lead in monitoring physiological parameters of patients is well known to those skilled in the art and is not therefore described in detail herein. However, highly preferred embodiments of the present invention employ multiple reference electrical connectors 14 (e.g., a set of up to four electrical connectors) for connection to multiple reference electrical leads 16 as desired. These multiple reference electrical connectors 14 are preferably electrically connected to the electrical port 30, amplifier 33, digitizer 31, and/or transmitter 35 as described earlier. The use of multiple electrical connectors 14 as reference electrical connectors is desirable in many applications for simplifying the process of changing a reference lead 16. For example, when it is determined by a user that a reference lead is performing unacceptably, the user can electronically switch between reference leads via a computer, controller, or other conventional device electrically connected to the jackbox circuitry (via electrical wiring or wireless transmission). This avoids the need to connect another reference electrical lead to the jackbox 10 and/or to apply another reference electrical lead to the patient (which can interrupt or disturb the monitoring process, can interfere with ongoing surgery, etc.). As another example, each reference lead can be associated with and compared to one or more electrical leads 16 running from the patient (such as a scalp reference lead and a depth reference lead associated with a number of scalp and depth electrical leads 16, respectively. As yet another example, multiple reference electrical connectors 14 can be used to connect a single reference electrical lead 16 to multiple jackboxes 10. This provides the ability to "remontage" data from selected electrical leads (permitting comparison, for example, between signals from one or more electrical leads) or to digitally create data based upon data acquired from different amplifiers.

Preferred embodiments of the present invention employ space saving arrangements of electrical connectors 14 and electrical leads 16 to help minimize jackbox size. These arrangements can be generated by mounting electrical connectors 14 in a number of ways within the enclosure 12 and/or by providing for movement of the electrical connectors 14 within the enclosure 12. The preferred embodiment of the present invention illustrated in FIGS. 1–7 utilizes both of these space saving techniques as will now be described.

With reference to FIGS. 3 and 4, the electrical connectors 14 are preferably arranged in sets as described above. Preferably, these sets are each a series of side-by-side electrical connectors in a substantially straight line. Although any number of sets can be used in the jackbox 10, the jackbox 10 preferably has two sets attached to the base 20 (front base set 46 and rear base set 48) and two sets attached to the lid 22 (front lid set 50 and rear lid set 52). The front sets 46, 50 are preferably spaced a sufficient distance from the rear sets 48, 52 to permit the ends 40 of the electrical leads 16 to fit between the front and rear sets 46, 48 and 50, 52. The preferred positions taken by the electrical connectors 14 and leads 16 in the closed position of the enclosure 12 are best shown in FIGS. 3 and 5–7. To help optimize space within the enclosure 12, the electrical connections 18 are nested within one another. Specifically, the lid and base front sets 46, 50 are preferably nested within one another, as are the lid and base rear sets 48, 52. The capability to nest is, of course, dependent upon the shape of the electrical connections 18 and the distance between adjacent electrical connections 18 in the same set. Nesting is accomplished in the illustrated embodiment by the round cross section of the electrical lead ends 40 and by the fact that adjacent leads 16 connected to the same set are spaced a distance from one another. Most preferably, the top sets of electrical connectors 18 are substantially aligned between the bottom sets of electrical connectors as is best shown in FIG. 7.

By consciously nesting electrical connections 18 in the present invention's design, the space occupied by the electrical connections 18 within the jackbox 10 can be conserved. The overall size of the jackbox 10 can therefore be significantly reduced, making the jackbox easier and more comfortable to wear and taking up less space in a patient's surroundings (both highly desirable as discussed above).

The term "nesting" as used herein and in the appended claims means that at least some portion of an electrical connection 18 (electrical lead end 40 connected to an electrical connector 14) is at least partially located between at least some portion of adjacent electrical connections 18 by conscious design. For example, the electrical lead ends 40 and associated electrical connectors 14 in one set can both be located at least partially between electrical lead ends 40 and associated electrical connectors 14 in another set. Alternatively, just the electrical leads ends 40 or just the electrical connectors 14 in one set can be located at least partially between electrical lead ends 40 and associated electrical connectors 14 in another set. In still other embodiments, just the electrical leads 40 (see FIGS. 1–7) or just the electrical connectors 14 of adjacent sets can be nested together. Any of these configurations create space savings within the enclosure.

The term "nesting" as used herein and in the appended claims does not necessarily mean that one set of electrical connections 18 completely overlaps another. Specifically, one set of electrical connectors can only partially overlap another, such as a part of the electrical connectors 14 in the front lid set 50 partially overlapping a part of the electrical lead ends 40 in the lid as best shown in FIG. 7. It should be noted that the terms "overlap" and "overlapping" as used herein and in the appended claims do not indicate or imply any particular orientation of the sets 46–52, enclosure 12, or jackbox 10. Any of all of these elements are positionable in virtually any desired orientation (vertically, horizontally, diagonally, etc.) in a stationary or mobile patient monitoring system whether worn on the patient or not.

In other preferred embodiments of the present invention, one set of electrical connections can be nested within two, three, or even more other sets. For example, to conserve space in the most preferred embodiment of the present invention shown in FIGS. 1–7, the front lid set 50 of electrical connections 18 is nested within the front base set 46 and within the rear lid set 52. Similarly, the front base set 46 of electrical connections 18 is nested within the front lid set 50 and the rear base set 48. Therefore, space conservation can be achieved in preferred jackbox embodiments according to the present invention by nesting sets in various manners, whether by overlapping one set of electrical connectors 18 substantially entirely with respect to another or by only partially overlapping such sets or by overlapping in both ways.

Another manner in which to conserve space within the jackbox 10 is by efficient organization of the electrical leads 16 and the paths through which they run in the jackbox 10. As can best be seen with reference to FIGS. 2, 4, 5 and 7, electrical connections 18 in one set are preferably offset with respect to electrical connections 18 in adjacent sets. This not only facilitates the nesting described above, but also provides electrical lead feed paths when sets of electrical connections 18 are positioned one before another in the jackbox 10. Electrical leads 16 running to the rear base and lid connector sets 48, 52 in the illustrated preferred embodiment of the present invention pass between the nested front base and lid connector sets 46, 50. In such case, each lead 16 running to a rear set preferably passes through an aperture 54 defined by adjacent electrical connections 18 of the front sets 46, 50. The electrical connectors 14 in the front sets can be shaped in a number of different ways to increase the size of these apertures 54, such as by flats 56 on the facing exterior surfaces of these connectors 14 (as best shown in FIG. 7), by less pronounced curved facing exterior surfaces of these connectors 14, etc. The apertures 54 are preferably large enough to accommodate the number of leads 16 passing therethrough, which in the case of the illustrated preferred embodiment is one lead 16 per aperture 54, but which can be two or more leads depending upon the number of connections 18 located behind the sets in question.

It should be noted that wire lead paths from connections 18 located behind one or more other connections 18 preferably exist as described above even where the front connections are not nested with rear connections as described above. In these cases, as with the embodiments described above and illustrated in the drawings, front connections 18 and rear connections 18 are most preferably offset with respect to one another so that the rear connections 18 are substantially aligned with a plane passing between front connections 18 (to provide a relatively straight path from the rear connections 18 to the outside of the jackbox 10). Such an arrangement not only provides improved organization of electrical leads 16 in the jackbox 10, but also lessens strain upon the electrical leads 16, the ends 40 thereof, and the electrical connectors 14. The nesting and offset features of the electrical connections 18 just described are also helpful in protecting the electrical leads 16 from being bent through an excessive radius of curvature as they pass through and out of the jackbox 10. Such excessive bending can be damaging to the electrical leads 16 and their ends 40. To further protect against excessive lead bending, the surfaces adjacent to the electrical leads 16 (especially near their respective connection to the electrical connectors 14) can be smoothed, radiused, and/or rounded. Such shaping can take a number of different forms, and in some highly preferred embodiments is gradual, such as a non-constant radiused rear shape of front electrical connectors 14. Such shaping can best be seen by way of example in the embodiment of the present invention shown in FIGS. 8–12.

In addition to the various relative positions of the electrical connector sets 46–52 discussed above, the relative angles of the sets 46–52 and connections 18 with respect to one another can also vary significantly by conscious design. In the preferred embodiment of the present invention shown in the figures, the front base and lid sets 46, 50 are not parallel with respect to one another, but instead are angled toward one another to converge toward the front of the jackbox 10. Similarly, the rear base and lid sets 48, 52 are preferably angled toward one another to converge toward the front of the jackbox 10. This relationship not only improves the ability of the front sets 46, 50 to nest with the rear sets 48, 52, but also orients the leads 16 toward the lead aperture 58 in the front of the enclosure 12 (described in more detail below) and better orients the leads 16 running from the rear sets 48, 52 between the front sets 46, 50. Orienting the leads in this manner helps reduce strain upon the electrical leads 16, the electrical lead ends 40, and the electrical connectors 14. In alternative embodiments of the present invention, the sets 46–50 can be oriented in different manners with respect to one another, such as one or both top and bottom sets being substantially parallel to one another (and together oriented at any desired angle toward the front of the enclosure 12), angled away from each other in a direction toward the front of the jackbox, etc. These different orientations of the sets 46–50 with respect to one another can call for different electrical lead paths and different locations of the lead aperture 58.

It should be noted that although it is preferred to nest all electrical connectors 18 within other electrical connectors 18 (whether wholly or partially) to conserve space and for other purposes to be described below, any fraction of the electrical connectors 18 in the jackbox can be nested as desired. In less preferred embodiments of the present invention, none of the electrical connectors 18 are nested. Also, it is possible to employ electrical connector arrangements in which electrical connections 18 located one in front of the other are not offset as described above.

The preferred embodiment of the present invention illustrated in FIGS. 1–7 has four sets of electrical connectors 14 arranged and oriented to nest two pairs of electrical connections 18, one pair in front of the other. One having ordinary skill in the art will appreciate that the present invention can be practiced with different numbers of electrical connectors 14 and electrical connections 18. For example, alternative embodiments of the present invention can have one, two, or three of the four sets of electrical connectors 14 removed. In one embodiment, a jackbox has only two sets of nesting electrical connections 18 on its lid 22. In another embodiment, two front nesting electrical connections 18 are mounted on a base 20 and lid 22, respectively. Also, any number of additional sets can be added in larger jackboxes in a nesting or non-nesting relationship as desired. Preferably (although not necessarily) in each case, electrical connectors 14 are still offset with respect to other electrical connectors 14 therebehind for the reasons described above.

An optional feature of the present invention regards the retention of the electrical leads 16 in the jackbox 10. To prevent inadvertent disconnection of the electrical leads 16, the electrical connectors 14 are preferably positioned within the jackbox 10 so that when the jackbox 10 is in its closed position, the electrical leads 16 are physically blocked against disconnection and removal from the electrical connectors 14. This function is preferably accomplished by positioning one or more jackbox elements adjacent to the ends 40 of the electrical leads 16 when the jackbox 10 is in its closed position. Because the ends of electrical leads 40 are usually enlarged as mentioned above, their size can be used to prevent them from being removed from their connected positions when the jackbox 10 is closed. The jackbox elements preventing such removal can be other electrical connectors 14, other electrical leads 16, a retaining element integral with or coupled to the enclosure 12, and the like. Although preferred, nesting of electrical connections 18 (or any part thereof) is not required to accomplish this feature of the present invention.

In the preferred embodiment of the present invention illustrated in FIGS. 1–7, the rear base and lid sets 48, 52 are positioned a distance from the front base and lid sets 46, 50 sufficient to receive the enlarged ends 40 of the electrical leads 16 coupled to the rear base and lid sets 48, 52. This distance is preferably sufficient to receive the enlarged ends 40 with a light clearance to the front base and lid sets 46, 50. When the jackbox 10 is closed (described in more detail below), these enlarged ends 40 are therefore blocked against disconnection by the front base and lid sets 46, 50. Although the distance between the front and rear sets can be slightly larger if desired, this distance is preferably insufficient to break electrical contact between the electrical leads 16 and their corresponding electrical connectors 14. As an alternative to the abovedescribed retaining arrangement, the electrical leads 16 running to the rear base and lid sets 48, 52 can be located adjacent to the electrical leads 16 running to the front base and lid sets 46, 50 so that the enlarged ends 40 of the leads 16 running to the front base and lid sets 46, 50 block the enlarged ends 40 of the leads 16 running to the rear base and lid sets 48, 52 from disconnection. In turn, the leads 16 running to the front base and lid sets 46, 50 can be blocked from disconnection by one or more retaining elements as described below.

The preferred embodiment of the present invention illustrated in FIGS. 1–7 also has retaining elements 60 located at the front of the jackbox 10. These retaining elements 60 are preferably separate elements attached to the inside front surfaces of the base 20 and lid 22 in any conventional manner (e.g., by conventional fasteners, adhesive, cohesive, mating joints, and the like). Alternatively, the retaining elements 60 can be integral with the base 20 and lid 22. The retaining elements 60 are preferably block-shaped elements positioned a distance from the front base and lid sets 46, 50. This distance is preferably sufficient to receive the enlarged ends 40 of the electrical leads 16 coupled to the front base and lid sets 48, 50 with a light clearance to the retaining elements 60. When the jackbox 10 is closed (described in more detail below), these enlarged ends 40 are therefore blocked against disconnection by the retaining elements 60. Although the distance between the front sets 46, 50 and the retaining elements 60 can be slightly larger if desired, this distance is preferably insufficient to break electrical contact between the electrical leads 16 and their corresponding electrical connectors 14.

It should be noted that the retaining elements 60 can take a number of different shapes and can be made of a number of different materials. Rather than the block-shaped elements illustrated in the figures, each retaining element 60 can be one or more pins, posts, ridges, flanges, bumps, bars, or other elements located the above-described distance from the front base and lid sets 48, 50 and attached to the enclosure 12 in any conventional manner or integral therewith. The retaining elements 60 in the illustrated preferred embodiment can be replaced by one retaining element attached to or integral with the base 20 or the lid 22 and sized to perform the same functions as the multiple retaining elements described herein. If desired, the retaining elements 60 can be shaped to fit the electrical leads 40 and/or the ends 40 thereof. The retaining elements 60 are preferably made of a resilient deformable material such as foam, rubber, urethane, sponge, and the like. However, the retaining elements 60 can instead be made from any resilient material, including without limitation plastic, metal, composites, ceramics, etc.

In highly preferred embodiments of the present invention, the retaining elements are used not only to block the electrical leads 16 from disconnection as described above, but also to help keep the electrical leads 16 from shifting, bundling, and tangling. Specifically, the electrical leads 16 preferably run from the electrical connectors 14 out of the jackbox 10 through the lead aperture 58 of the jackbox 10 in an organized (and most preferably, substantially parallel) manner. When the jackbox 10 is in its closed position shown in FIGS. 1, 3, and 5–7, the electrical leads 16 are preferably trapped between the retaining elements 60 or between a retaining element 60 and an inside surface of the enclosure 12. Resilient and deformable retaining elements 60 are most preferred to compress the electrical leads 16 between the retaining elements 60 (or between a retaining element 60 and the enclosure 12) with significant force but without stressing the leads 16 or the lead ends 40. Other retaining element materials mentioned above can instead be used to press and hold the electrical leads 16 and/or the ends 40 thereof.

In less preferred embodiments of the present invention, the compressive force exerted upon the leads 16, their ends 40, or upon both the leads 16 and their ends 40 by the retaining elements 60 is great enough to block the transmission of pulling force upon the leads 16 exterior to the jackbox 10. As will be appreciated by one having ordinary skill in the art, this increased force can be generated by enlarging the retaining elements 60, by using a more resilient retaining element material, etc. Where such increased retaining force is used, the need for the set arrangement described above to prevent lead disconnection (one set of leads 16 blocked from disconnection by another set of leads 16 or by a set of electrical connectors 14) is lessened or obviated.

In the preferred jackbox embodiment illustrated in FIGS. 1–7, the retaining elements 60 are located at the front of the enclosure 12 to interfere with removal of leads 16 connected to the front sets of electrical connectors 14. Retaining elements such as those described above can also or instead be located adjacent to any other connectors 14 in the jackbox for accomplishing this same purpose. By way of example only, one or more retaining elements can be attached to or extend from the interior surfaces of the base 20 and lid 22 to retain electrical leads 16 running to the rear base and lid sets of electrical connectors 14. Such retaining elements are preferably substantially the same and operate in substantially the same manner as those described above.

As just described, the electrical leads 16 in the various embodiments of the present invention are preferably retained in connection with the electrical connectors 14 by interference with other electrical leads 16, other electrical connectors 14, or one or more retaining elements 60. More than one of these elements can cooperate to block disconnection when the jackbox 10 is closed. Depending upon the location and arrangement of the electrical connectors 14 and leads 16 in the jackbox 10, any one or more electrical leads 16 can be blocked from disconnection by combined interference with one or more electrical connectors 14, electrical leads 16, and/or retaining elements 60. For example, a rear set of electrical leads 16 can be blocked from disconnection by combined interference with a set of electrical leads 16 nested within a set of electrical connectors 14, or can be blocked from disconnection by combined interference with a set of electrical connectors 14 and an adjacent retaining element 60. Such combinations of elements used to prevent lead disconnection depends at least partially upon the arrangement and orientation of electrical connectors 14 within the jackbox 10 (various arrangements and orientations being possible as described above). Also, although the preferred embodiment of the jackbox 10 shown in FIGS. 1–7 have only two levels of electrical connections 18 (front and rear), the manners described above for nesting the electrical connections 18 and for retaining the electrical leads 16 can be employed for any number of connector levels arranged separately, in sets, clusters, or in any other fashion.

The enclosure 12 of present invention can preferably be opened and closed for access to the electrical connectors 40 and for connecting and disconnecting the electrical connections 18. When the enclosure 12 is in its closed position shown in FIGS. 1, 3, and 5–7, the electrical leads 16 preferably run out of the enclosure 12 via the lead aperture 58. The lead aperture 58 most preferably is elongated and relatively thin, and most preferably is about the same thickness as the diameter of an electrical lead 16. Therefore, leads 16 exit from the enclosure 12 in a side-by-side relationship.

The lead aperture 58 is defined by the base 20 and lid 22 in the illustrated preferred embodiment, but can instead be defined by any two adjacent and movable elements making up the enclosure 12 or can be fully located in the base 20, lid 22, or other element making up the enclosure 12. Furthermore, more than one lead aperture can be used, and can be located virtually anywhere on the enclosure 12, if desired. The ability to use one or multiple lead apertures located in this manner facilitates the use of different enclosure types from the preferred clamshell enclosure of the preferred embodiment illustrated in FIGS. 1–7. For example, if the electrical connectors 14 were oriented toward one or both sides of the enclosure 12 illustrated in the figures (rather than toward the front of the enclosure 12), lead apertures 58 and corresponding retaining elements 60 could be located along the enclosure sides to permit exit of the leads 16. In such an embodiment, the enclosure 12 would open as a book rather than as a clamshell. In another possible embodiment, electrical connectors 14 are oriented toward the sides and edges of the enclosure 12 through which the electrical leads 16 pass. Other enclosure shapes and other electrical connector orientations therein can call for still other lead aperture locations and arrangements.

As noted above, the substantially flat jackbox design described above and illustrated in the figures is preferred because it provides for a compact design and does not protrude far from a wearer's body. Also, where the electrical leads 16 run from the front or edges of the enclosure 12, the leads 16 are substantially parallel and close to the wearer's body. In the illustrated preferred embodiment of the present invention, the electrical leads 16 run in the same direction (preferably vertically but possibly horizontally or in other directions) through the lead aperture 58 and substantially parallel to the wearer's body. Because the electrical port 30 is substantially parallel to the electrical leads 16 in this embodiment, connection to the jackbox 10 via this port 30 is also kept close to the wearer's body. These relationships between the enclosure 12, the electrical leads 16 and the electrical port 30 keep the jackbox 10 and associated wiring to a minimally obtrusive level and provides comfort and ease in wearability. One having ordinary skill in the art will recognize that it is possible to employ electrical connectors 14 oriented toward the top and bottom of the enclosure 12 (rather than to one or more edges as described above) for connection to electrical leads 12 passing through one or more apertures in the base 20 and the lid 22. However, the embodiments of the present invention described above are preferred based at least partially upon their space saving advantages, ability to nest electrical connections, and electrical lead retention features.

Another way to minimize jackbox size in the present invention is to provide for movement of the electrical connectors 14 within the enclosure 12. Although it is possible to reduce jackbox size in the present invention by arranging and orienting the electrical connectors 14 (and therefore, the electrical leads 16 and electrical connections 18) in various manners, many size-minimizing arrangements and orientations do not offer easy or convenient user access to the electrical leads 16 and their ends 40. To address this problem, preferred embodiments of the present invention have electrical connectors 14 mounted for movement between a storage position and a user access position. In the storage position, the electrical connectors 14 are arranged and oriented to minimize the size of the jackbox 10 while in the user access position, the electrical connectors 14 are arranged and oriented to maximize a user's ability to access, connect, and disconnect electrical leads 16.

Referring again to FIGS. 1–7, the preferred embodiment of the present invention illustrated therein employs a linking mechanism 62 for automatically moving all sets 46–52 of electrical connectors 14 from a storage position to a user access position simply by opening the jackbox clamshell. The linking mechanism 62 preferably has two pairs of linking elements, one pair 64, 66 connected to the base sets 46, 48 of electrical connectors 14 and one pair 68, 70 connected to the lid sets 50, 52 of electrical connectors 14. The sets 46, 48, 50, 52 are preferably pivotably connected at opposite ends to the linking elements 64, 66, 68, 70. The linking elements 64, 66, 68, 70 are preferably pivotably connected to the lid 22 in any conventional manner near the jackbox hinge 24. Specifically, the linking elements 64, 66 connected to the base sets 46, 48 of electrical connectors 14 are preferably pivotably mounted to the lid 22 at the rear of the enclosure 12, while the linking elements 64, 66 connected to the lid sets 50, 52 are preferably pivotably connected to the base linking elements 64, 66 also near the rear of the enclosure. Therefore, by opening enclosure 12, the base linking elements 64, 66 automatically are pulled a distance in a rearward direction (toward the hinge 24 of the enclosure 12) by the lid 22 while the lid linking elements 68, 70 are pulled in the same direction by their connection to the base linking elements 64, 66.

The linking element motion just described is used to move the electrical connectors 14 from the storage position shown in FIGS. 1, 3, and 5–7 to the user access position shown in FIGS. 2 and 4. In the preferred embodiment of the present invention shown in these figures, this is done by pivotably mounting the sets of electrical connectors 46, 48, 50, 52 not just to the linking elements 64, 66, 68, 70, but also to the enclosure 12. Specifically, the front and rear base sets 46, 48 are preferably pivotably coupled at their ends to the base 20 at locations disposed from their connection points to the base linking elements 64, 66, while the front and rear lid sets 50, 52 are preferably pivotably coupled at their ends to the lid 22 at locations disposed from their connection points to the lid linking elements 68, 70. The sets of electrical connectors 46, 48, 50, 52 therefore pivot about their connections to the enclosure 12 when the linking elements 64, 66, 68, 70 are moved (which movement is preferably generated by opening the enclosure). By pivoting the electrical connectors 14 in this manner, the electrical connections 18 can be closely arranged to optimize space in the closed jackbox 10 even if such an arrangement provides little to no user access to the electrical connections 18. Also, the electrical connections 18 in the open jackbox 10 can be arranged in a widely spread position even if such an arrangement significantly increases jackbox size in the open position.

When the enclosure of the highly preferred jackbox embodiment shown in FIGS. 1–7 is opened, the sets of electrical connectors 14 are pointed in the same general direction (with the exception of possible slight convergence or divergence of the directions depending upon the positions of the connection between the linking element 64, 66, 68, 70, sets of electrical connectors 14, and the enclosure 12). Because the sets 46, 48, 50, 52 have preferably been pivoted from their storage positions, the shortest distance between neighboring sets has been increased and the electrical leads 16 have been spread apart or "fanned" for increased user access.

The linking elements 64, 66, 68, 70 are preferably made of resilient plastic material, but can instead be made out of any resilient material (including without limitation steel, aluminum, and other metals, composites, ceramics, and the like) capable of performing the functions described above. Also, because the linking elements 64, 66, 68, 70 are each preferably relatively elongated and thin members, they take up little space in the jackbox 10. Because the motion of one or more linking elements 64, 66, 68, 70 can cause interference between the linking elements 64, 66, 68, 70 and the enclosure 12, electrical connectors 14, or other elements of the jackbox 10, any or all of the linking elements 64, 66, 68, 70 can be shaped to avoid such interference. For example, in the preferred embodiment of the present invention shown in FIGS. 1–7, the linking elements 64, 66, 68, 70 have portions shaped to avoid interference with the pivot connection between the sets of electrical connectors 14 and the enclosure 12.

Depending at least partially upon the shape of the enclosure, the shape and position of the linking elements 64, 66, 68, 70, and the positions of the electrical connectors 14 in the jackbox 10, it can be desirable to employ linking elements 64, 66, 68, 70 that are jointed or that otherwise have portions movable with respect to one another. For example, one or more of the linking elements 64, 66, 68, 70 can be made of multiple elements pivotably connected together in a conventional manner. As another example, one or more of the linking elements 64, 66, 68, 70 can have one or more portions of reduced thickness or otherwise weakened portions permitting linking element bending thereabout ("live hinges"). The linking elements 64, 66, 68, 70 in the preferred embodiment of the present invention shown in FIGS. 1–7 have live hinges 72 adjacent to the rear set pivot connections for permitting the live hinges 72 to clear the pivot connections of the rear sets 48, 52 to the base 20 and lid 22, respectively. The use of live hinges is at least partially dependent upon the material of the linking elements 64, 66, 68, 70, and so therefore is more applicable for linking elements 64, 66, 68, 70 made from a somewhat resiliently deformable material such as plastic, nylon, and the like. By employing linking elements 64, 66, 68, 70 that are jointed or that have live hinges, the linking elements 64, 66, 68, 70 can collapse into positions otherwise inaccessible by other linking elements, thereby saving critical space within the jackbox 10.

Each of the pivoting connections described above (between the sets of electrical connectors 14 and the linking elements 64, 66, 68, 70, between the linking elements 64, 66, 68, 70 and the enclosure 12, between the sets of electrical connectors 14 and the enclosure 12) is preferably conventional in form and operation, and most preferably is a simple conventional pin and socket connection. The pins can be separate elements passed through holes in the connected elements and secured therein in any well known manner (by flanged ends, snap fits, and the like), can be integral with or fastened in any conventional manner to either one of the connected elements for pivotal movement of the other connected element thereabout, etc. However, any other pivot elements and assemblies well known to those skilled in the art can be used to establish the above-described connections.

The angles at which the electrical connectors 14 are positioned when the enclosure 12 is opened can be changed from the preferred positions shown in the figures. These angles can be changed, for example, by pivotably connecting the base linking elements 64, 66 to different locations on the lid 22, by pivotably connecting the base linking elements 64, 66 to different locations on the lid linking elements 68, 70, by changing the distance between the points at which the sets of electrical connectors 14 are pivotably attached to the enclosure 12 and the points at which these sets are pivotably attached to the linking elements 64, 66, 68, 70, and the like.

In one illustrated preferred embodiment of the present invention, the lid linking elements 68, 70 are pivotably connected to the base linking elements 64, 66, which are in turn pivotably connected to the lid 22 of the enclosure 12. In an alternative embodiment of the present invention, the base linking elements 64, 66 are pivotably connected to the lid linking elements 68, 70, which are in turn pivotably connected to the base 20 of the enclosure. In another alternative embodiment, the base linking elements 64, 66 and the lid linking elements 68, 70 are not connected together, but are instead pivotably coupled to the lid 22 and the base 20, respectively, in a conventional manner near the rear of the enclosure 12. It yet another alternative embodiment, none of the base or linking elements 64, 66, 68, 70 are directly connected to the enclosure, but are instead pivotably connected to the sets of electrical connectors 14 as described above and are pivotably connected to one another (base linking elements 64, 66 to lid linking elements 68, 70). One having ordinary skill in the art will appreciate that still other arrangements are possible in which opening of one or more enclosure elements transmits motive force to linking elements. The particular connection points of the linking elements in these other arrangements is at least partially dependent upon the shape of the enclosure and the manner in which the enclosure elements move to open the enclosure. Each of the alternative embodiments still functions to transmit an enclosure opening motion to motion of the linking elements 64, 66, 68, 70 (which in turn can be transmitted to the electrical connectors 14 as described above), and falls within the spirit and scope of the present invention.

Although linking element motion is preferably generated by respective movement of the base 20 and lid 22 as described above, linking element motion can be generated by relative motion of any part of the enclosure 12 regardless of enclosure shape. Enclosures not having a clamshell shape can still employ one or more linking elements connected between a portion of the enclosure and one or more electrical connectors 14 movable relative thereto to transmit enclosure motion to electrical connector motion in any manner such as those described above. For example, the enclosure can be a box having a door defining any portion thereof and to which one or more linking elements are connected. These linking elements can be connected to one or more electrical connectors 14 within the enclosure to move them in response to movement of the door. This and other alternative arrangements fall within the spirit and scope of the present invention. It will be appreciated by one having ordinary skill in the art that such alternative arrangements are not dependent upon a particular enclosure shape or size, nor are they dependent upon the shape or size of enclosure portion movable to gain access to the electrical connectors 14 inside.

Less preferred embodiments of the present invention do not transmit motion of any portion of the enclosure 12 to the electrical connectors 14. Motion of the electrical connectors 14 can instead be generated by directly moving one or more of the linking elements 64, 66, 68, 70 (e.g., by user manipulation of one or more linking elements 64, 66, 68, 70, user manipulation of a lever, handle, or other user-accessible element coupled to one or more of the linking elements 64, 66, 68, 70, etc.).

In highly preferred embodiments of the present invention such as the embodiment shown in FIGS. 1–7, all of the electrical connectors 14 are movable (via linking elements) in response to opening or closing the enclosure 12. However, any number of electrical connectors 14 can be mounted within the enclosure 12 in this manner if desired. In alternative embodiments of the present invention, any one or more or portion of the sets 46, 48, 50, 52 can be mounted in the enclosure 12 without being connected to any linking elements 64, 66, 68, 70, without the capacity to move, or can be movable only by user manipulation of the sets 46, 48, 50, 52 or linking elements 64, 66, 68, 70 as discussed above.

With reference again to the preferred embodiment of the present invention illustrated in FIGS. 1–7, motion of the electrical connectors 18 between a storage position and a user access position is preferably accomplished by causing the electrical connectors 14 to rotate as described above. However, increased user access can be achieved in other manners of moving the electrical connectors. For example, rather than being coupled to the enclosure 12 at pivot points, the sets 46, 48, 50, 52 can be coupled thereto by conventional pin and groove connections in which the sets 46, 48, 50, 52 translate or slide within the enclosure 12 when opened. The electrical connectors 14 therefore spread apart within the enclosure 12 by translation rather than rotation as described above. Such movement can be generated by employing any of the same motion transmitting arrangements described above, but most preferably is generated by linking elements coupled to the sets 46, 48, 50, 52 to pull and push the sets through a range of sliding positions as the enclosure 12 is opened or closed. One having ordinary skill in the art will appreciate that the translational relationship between the sets of connectors 14 and the enclosure can be accomplished in many well known manners, such as by slides, tracks, rails, guides, and the like connecting the sets of connectors 14 to the enclosure 14.

As another example, it is also possible to employ the translational movement just described with the rotational movement described above to both translate and rotate the sets of electrical connectors 14 by opening or closing the enclosure 12. Once again, such movement can be generated by employing any of the same motion transmitting arrangements described above, but most preferably is generated by linking elements coupled to the sets 46, 48, 50, 52 to slide or translate the sets 46, 48, 50, 52 before, while, or after they are rotated.

Most preferred embodiments of the present invention utilize linking elements that are coupled to the ends of the sets of electrical connectors 14 as described above, and that are relatively thin and elongated in shape. However, it should be noted that the shape, number, and position of the linking elements can be significantly different from those described above and shown in the figures while still functioning in the same manner. For example, the linking elements need not necessarily be located on the ends of the sets 46, 48, 50, 52. Instead or in addition, one or more linking elements can be located anywhere on the sets, such as through the middle of the sets (but preferably not interfering with electrical lead paths and electrical connector motion), between the sets 46, 48, 50, 52 and the enclosure 12, etc. Such alternative manners of connection can be particularly useful for embodiments of the jackbox 10 not employing rows of electrical connectors 14 as in the illustrated preferred embodiment. The linking elements in alternative embodiments need not necessarily be elongated and thin, but depending upon space constraints can be in strip, wire, or other form as desired. Also, alternative embodiments of the present invention can employ fewer or more linking elements, such as linking elements located only on one end of each set, dedicated linking elements for single electrical connectors 14 or electrical connectors 14 in groups of two or more, three or more linking elements per set, and the like. Furthermore, each linking element need not connect multiple electrical sets together as described above, but can instead be connected only to the enclosure (or other linking element) and a set of electrical connectors 14. Each set can even have its own dedicated linking element or elements. Motion can also be transmitted between electrical connectors 14 or sets thereof by linking elements that are only coupled therebetween and not to the enclosure or other linking elements.

Although linking elements such as those described above and illustrated in the drawings are the preferred manner to transmit motion of the enclosure 12 to motion of the electrical connectors 14 for moving the electrical connectors 14 from a storage position to a user access position, one having ordinary skill in the art will appreciate that such elements are not the only way to transmit this motion. For example, this motion can be transmitted by one or more cam follower elements connected between the hinge 24 of the enclosure 12 and the rear portions of the sets 46, 48, 50, 52. The hinge 24 (or element attached thereto) in such an embodiment acts as a cam, preferably having an outer surface that is eccentric with respect to the hinge pivot axis.

When the hinge 24 is pivoted as the enclosure 12 is opened or closed, the riding cam follower elements are pushed or pulled, thereby pushing or pulling the rear portions of the sets 46, 48, 50, 52. The sets 46, 48, 50, 52 can thereby be translated or rotated to various positions as desired.

As another example, each of the sets 46, 48, 50, 52 can be pivoted into user access positions when the enclosure 12 is opened by one or more conventional elastic elements connected between sets that are adjacent to one another when the enclosure is closed or between a set and an enclosure surface opposite the set (e.g., connected between the lid and a base set or between the base and a lid set). These elastic elements can be extension springs or like elements, and preferably exert sufficient force upon the electrical connectors 14 to pivot them into the positions shown in FIGS. 2 and 4 as the enclosure 12 is opened, but which do not exert sufficient force to close the enclosure 12 once opened. To return the electrical connectors 14 to their storage positions when the enclosure 12 is closed, one or more biasing springs can be connected to each of the sets 46, 48, 50, 52 in any conventional manner. Such springs can be torsion, compression, extension, leaf, or any other springs capable of biasing the sets 46, 48, 50, 52 into the positions shown in FIGS. 1, 3, and 5–7, but most preferably are torsion springs connected to the sets 46, 48, 50, 52 at their pivoting ends.

As yet another example of alternative designs for moving the electrical connectors 14 between storage and user access positions, the linking elements 64, 66, 68, 70 of the preferred embodiment described above and illustrated in FIGS. 1–7 can be replaced by one or more scissor linkages connected in a conventional manner between the base and lid sets of electrical connectors 14. Such linkages can be pivotably connected indirectly or directly to the base and lid sets in the manner as described above for the linking elements 64, 66, 68, 70. These linkages preferably exert a pulling force upon the base and lid sets as the enclosure 12 is opened to pivot, translate, or both pivot and translate the sets (see above) to a spread position, and preferably exert an opposite force as the enclosure 12 is closed to pivot, translate, or both pivot and translate the sets to their storage positions 12. Still other conventional mechanisms and assemblies for moving the electrical connectors 14 in response to opening or closing of the enclosure 12 are possible and would be recognized by one having ordinary skill in the art. As such, these and the above alternative designs fall within the spirit and scope of the present invention.

To make the process of connecting and disconnecting electrical leads 16 easier in the present invention, it is desirable (though not required) to provide some manner to visually distinguish one electrical connector 14 from the others. This can be done in a number of different manners, including without limitation using differently colored electrical connectors 14, indicia for each electrical connector 14 stamped, printed, molded, painted, decaled, embossed, or otherwise marked upon the electrical connectors 14, upon portions of the jackbox 10 adjacent to the electrical connectors (preferably at least when in the open position), or upon labels attached adjacent to the electrical connectors 14 as shown in FIG. 2. One or more surfaces of the electrical connectors 14 and/or portions of the jackbox 10 adjacent thereto can even be made of a material that can be directly written upon (preferably erasably) by a user, if desired. Although any conventional manner can be used for applying, forming, attaching, or otherwise associating some type of distinct indicia with each electrical connector 14, labels are most preferably used in the present invention. Not only do labels offer good-sized visual indicia, but they can be adapted for removal and replacement. The labels (not shown) can be stickers, cards, or other pieces of material of any shape and size having indicia thereon corresponding to the adjacent electrical connectors 14. Although the labels can be mounted directly upon the electrical connectors 14 in any conventional fashion, the labels are more preferably attached to indicia mounts 74 integral with the electrical connectors 14 or connected thereto in any conventional manner, such as by glue, conventional fasteners, snap-fitting into clips or grooves on the electrical connectors 14, pin and post connections between the mounts 74 and the electrical connectors 14, and the like. These indicia mounts 74 can be resilient strips of material, label frames, clips, or any other well known device capable of receiving and holding labels (each associated with one or more electrical connectors 14). The indicia mounts 74 of the highly preferred embodiment shown in FIGS. 1–7 are strips of material for each set of electrical connectors 14, and have edge clips to removably receive and hold labels upon the strips. Regardless of the type of label mounts used or the shape or size of the labels, the labels most preferably are removable and replaceable as desired so that the associated electrical connectors 14 can be assigned different or new indicia by the user based upon preference or application.

To further simplify the process of connecting and disconnecting electrical leads 16 in the present invention, the electrical leads 16 can also be labeled, marked, or otherwise adapted to be visually distinguishable from one another. This can be done in any conventional fashion used to label, mark, or otherwise distinguish wiring, such as by employing differently colored leads or lead ends, by stamping, printing, molding, painting, placing decals upon, or otherwise marking the electrical connectors with different indicia, etc. In highly preferred embodiments of the present invention, labels (not shown) are attached to the electrical leads 16 or to the ends 40 thereof. Most preferably, the labels are in the form of tape wrapped about the leads 16 or lead ends 40 or are sleeves fit about the leads 16 or lead ends 40. The sleeves can be colored or have indicia thereon, or can be transparent and trap indicia-bearing labels thereunder. One having ordinary skill in the art will appreciate that still other manners exist for labeling, marking, or otherwise distinguishing the electrical leads 16 from one another which fall within the spirit and scope of the present invention.

The embodiment of the present invention described above and illustrated in FIGS. 1–7 preferably has a resilient and non-deformable enclosure to protect the electrical connections 18 and circuitry in the jackbox 10. To make the jackbox 10 more comfortable to wear, it is of course possible to manufacture the enclosure and other jackbox elements from a semi-deformable or deformable material at the expense of greater potential stresses upon these jackbox elements. However, such "soft jackbox" embodiments more preferably employ features and elements that not only avoid such stresses, but also offer damage resistance (from impact, dropping, and other shock) that are superior to "hard jackbox" designs. These features and elements are described with reference to the highly preferred soft jackbox embodiment shown in FIGS. 8–12.

With the exception of the following description of soft jackbox elements and features, the soft jackbox 110 of FIGS. 8–12 shares the same features and elements of the hard jackbox of FIGS. 1–7, and has corresponding elements numbered in the 100 series. To illustrate the different possible configurations of the jackbox (whether in hard or soft form), the soft jackbox 110 is arranged to open like a book, and preferably has first and second body portions 120, 122 connected for relative pivotal motion about an edge defining a hinge 124. As with the hard jackbox 10, the location of the hinge 124 is most preferably at two adjacent edges of the first and second body portions 120, 122 (for maximizing access to the chamber 128 within the enclosure 112), but can instead be located inboard on one of the body portions 120, 122 if desired. The hinge 124 is preferably integral with the body portions 120, 122. Specifically, the body portions 120, 122 are preferably pivotably coupled together by a hinge 124 that is formed or molded with the body portions 120, 122. Such a hinge type can therefore be defined by a weakened area between the body portions 120, 122 or a portion of molded material that is more flexible than the adjacent body portions 120, 122. The hinge 124 can otherwise be made in a one-body enclosure 112 by removing enclosure material from the hinge location, scoring or grooving the hinge location, or otherwise weakening the hinge location to facilitate relative movement of the body portions 120, 122. Alternate embodiments of the present invention can employ any other conventional hinge design desired, including without limitation one or more flexible straps molded within and connecting the body portions 120, 122 or glued or conventionally fastened to the body portions 120, 122, one or more pivot pins or wires passed through mating apertures at the hinge location for pivotal movement of the body portions 120, 122 thereabout, posts formed on one body portion 120 for pivotably mating with apertures or hooks in the other body portion 122, etc. One having ordinary skill in the art will appreciate that still other manners of connecting the body portions for relative pivotal movement are possible and fall within the spirit and scope of the present invention.

The enclosure 112 is formed of a resilient semi-deformable or deformable material such as SANTOPRENE brand thermoplastic elastomer manufactured by Monsanto Company, other thermoplastic elastomer materials, urethane, rubber, soft plastic, and the like. However, subject to the ability to connect and disconnect electrical leads 116 to and from electrical connectors 114 in the jackbox 110 as will be described in more detail below, the enclosure can be made of virtually any resilient material (including those used for the hard jackbox 10). The enclosure 112 is therefore easily deformed by the user, whether for the purposes of electrical connection access, to contour to the body of the user, or to deform under impact or compression. The enclosure 112 is preferably formed in any conventional manner. As used herein and in the appended claims, the terms "formed" "forming" and "form" refer to and encompass any manner in which an element can be made, including without limitation blow molding, injection molding, extruding, casting, cutting, bending, shaping, pressing, and stamping.

Like the hard jackbox 10, the soft jackbox 110 has a number of electrical connectors 114. Electrical leads 116 can be releasably connected to the electrical connectors 114 to form electrical connections 118. Reference is made to the hard jackbox description above for more reference to the electrical connectors 114, their operation, and their alternative designs. The electrical connectors 114 are preferably arranged in groups or "sets" which most preferably are sets of side-by-side electrical connectors 114. The electrical connectors 114 in each set 146, 147, 148, 149, 150, 151 are coupled together in any conventional manner, such as by conventional fasteners, glue, snap fitting, soldering, etc., but most preferably share the same integral body (preferred also for the hard jackbox electrical connectors 14). This integral body is preferably made from a resilient semi-deformable or deformable material such as plastic, urethane, rubber, and the like, but in less preferred embodiments can instead be made from other resilient materials such as steel, aluminum and other metals, composites, and the like (at the possible expense of flexibility loss).

The soft jackbox 110 preferably has three sets of electrical connectors 114 in each body portion 120, 122 but can instead have any number in either body 120, 122, such as all in one body 120, 122, different numbers of sets in the bodies 120, 122, etc. Preferably, the electrical connectors 114 are mounted within the jackbox 110 by being molded into the enclosure 112. Specifically, the electrical connectors 114 are preferably molded into the material of the enclosure 112, which itself is preferably molded in any conventional form, including without limitation blow molding, injection molding, casting, and the like. The electrical connectors 114 can be shaped to facilitate or improve such molding and the strength of the electrical connector to enclosure attachment. For example, the electrical connectors 114 each preferably have a footing 161 about which the material of the enclosure 112 can be molded to hold the electrical connectors 114 in place. This footing 161 is preferably an enlarged shape and is most preferably an enlarged planar shape such as those shown in FIGS. 10 and 11 either integral with the material making up the electrical connectors 114 or attached thereto in any conventional manner. Additionally, the electrical connectors 114 preferably have apertures 163 for receiving enclosure material to further secure the electrical connectors 114 to the enclosure 112. The apertures are most preferably located within the footings 161 of the electrical connectors 114 and can be any shape, number or size desired. Most preferably however, each connector 114 is flanked by two oval or slot-shaped apertures 163 passing through its footing 161 to permit enclosure material to flow therethrough during the molding process.

The molding process is preferably a two-step process in which the enclosure material is applied to one side of the sets 146–151 and later is applied over the other side of the sets 146–151 to set them in the body portions 120, 122. As with any molding process employed in the manufacture of the soft jackbox 110, the electrical connectors 114 can be mounted within the jackbox 110 in sets of any number desired and/or can be individually mounted therein. Although not required, the tops of the electrical connectors 114 (above the footings) preferably remain exposed after the molding process. Molding processes are well known to those skilled in the art and are not therefore described further herein.

Although electrical connectors 114 are preferably molded within the enclosure 112, the electrical connectors 114 can instead be mounted within the jackbox 110 in a number of other well-known manners, including without limitation gluing individual or grouped electrical connectors 114 to the enclosure 112, fastening thereto via conventional fasteners such as rivets, threaded fasteners, mating snap fittings, pins and posts, clips and receptacles, etc.

The circuitry employed in the soft jackbox 110 is preferably substantially the same type as that described above with reference to the hard jackbox 10, and can be connected and take the alternative forms also described above. Flex circuits 134 coupled in a conventional manner to each of the electrical connectors 114 and to the electrical port 130 (which preferably has retaining elements such as port clips 132 described above), amplification circuitry, digitization circuitry, and/or wireless transmission circuitry are most preferred because they cooperate to ensure jackbox flexibility. If desired, the jackbox 110 can also be provided with a jackbox identifier 144 and power switch (not shown) preferably electrically connected by flex circuitry. The flex circuits 134 are preferably molded in the enclosure material in much the same manner as the electrical connectors 114, but can instead be attached to the enclosure 112 in any conventional manner, including without limitation gluing, fastening with conventional fasteners, and the like. As is the case in the hard jackbox 10, the flex circuits 134 can take any desired shape, but most preferably are shaped to be hidden from the user's view. If molded within the enclosure material 112, larger flex circuits 134 can be used such as those shown in FIGS. 10 and 11.

The electrical connectors 114 of the soft jackbox 110 can be arranged and oriented in any manner within the enclosure 112, but most preferably are arranged and oriented to save space, to secure the electrical connections 118 between the electrical leads 116 and the electrical connectors 114, and to provide and organized electrical lead arrangement in the jackbox 110 as all described with regard to the hard jackbox 10 above. A highly preferred electrical connector arrangement and orientation is employed in the soft jackbox 110 illustrated in FIGS. 8–12. In this embodiment, the electrical connectors 114 are arranged in offset rows and are oriented in substantially the same direction (toward the top of the jackbox 110). When the enclosure 112 is closed, the electrical connections 118 in one body portion 120 preferably nest within the electrical connections 118 in the other body portion 122 in a manner similar to the hard jackbox 110. Such an arrangement can be used with any number of electrical connector sets. Preferably, the electrical connectors 14 are oriented in a substantially parallel fashion, although slight convergence or divergence is possible for the purposes described above. In nesting, any portion or all of the electrical connections 118 in one body portion 120 (i.e., the ends 140 of the electrical leads 116 and/or the electrical connectors 114) can nest within any portion or all of the electrical connections 118 of another body portion 122.

Rows or sets of electrical connectors 114 in the same body portion 120, 122 that are located one in front of the other are preferably offset for the same purposes described above. Specifically, such an offset relationship provides much straighter electrical lead paths than in other arrangements, which helps to organize the electrical leads 116 and reduce the size of the jackbox, and facilitates improved nesting of one set of electrical connections 118 within the set in front of it. As shown in FIGS. 8–12, the electrical connections 118 of the rearmost sets 148, 151 preferably nest within the electrical connections 118 in the middle sets 147, 150, respectively, which in turn preferably nest within the electrical connections 118 in the front sets 146, 149, respectively.

Nesting of electrical connections 118 within the same body portion 120, 122 and between body portions 120, 122 is highly preferred because it also provides protection against disconnection of electrical leads 116 from electrical connections 118 when the jackbox 110 is closed. As with the hard jackbox 110 described above, the enlarged ends 140 of the electrical leads 116 in the bottom sets 147, 148, 150, 151 are blocked from disconnection by the electrical connections 118 above them. Most preferably, the enlarged ends 140 are blocked by the electrical connectors 114 above them, but any portion of the electrical connections 118 in front can be used to block against disconnection.

The soft jackbox 11 preferably also has retaining elements 160 performing the same functions as the retaining elements 60 in the hard jackbox 10. Preferably (although not necessarily), the retaining elements 160 are shaped to receive the enlarged ends 140 of the leads 116 closest to the top of the jackbox 110. Also, the retaining elements 160 preferably have dedicated lead apertures 158 therein (before each electrical connection 118 closest to the top of the jackbox 110) through which the electrical leads 116 pass out of the jackbox 110. However, the retaining elements 160 and the lead apertures 158 can take any form and arrangement as described above with regard to the hard jackbox embodiment. The preferred retaining element and lead aperture arrangement not only functions to retain the electrical leads 116 in connected relationship with the electrical connectors 114, but also to reduce the transmission of force and strain exerted by the electrical leads 116 being pulled from outside of the jackbox 110 when closed.

As with the hard jackbox 110 described above, it should be noted that electrical connector nesting, though preferred, is not required to practice the present invention. Also, offset connector sets can still be employed for the above-noted purposes without nested electrical connections 118.

To facilitate increased access to the electrical connections 118 in the preferred jackbox embodiment shown in FIGS. 8–12, the enclosure 112 is preferably deformable by a user. Preferably, both body portions 120, 122 can be bent by a user to better expose the electrical connections 118. With reference to FIG. 9 for example, the enclosure 112 is preferably bendable about axes A—A (which is preferably one of several or an infinite number of axes substantially parallel to axes A—A and about which the enclosure 112 is bendable) to spread or fan out the electrical connections 118 therein. This type of enclosure manipulation is desirable to permit easier electrical lead connection and disconnection with respect to the electrical connectors 114. In some embodiments of the present invention where the enclosure material is less flexible or where electrical connector nesting within the same body portion 120, 122 is fairly tight, such manipulation can even be needed.

To help facilitate enclosure deformation by a user as just described, the enclosure 112 can be notched, scored, or have areas of reduced thickness or in which enclosure material is removed. Each body portion 120, 122 of the enclosure 112 can even have two or more sections connected by joining elements that permit flexure or movement between the sections. These joining elements can be molded into the enclosure, attached thereto in any conventional manner (such as by glue or conventional fasteners), etc., and can take a number of different forms (such as strips of flexible material, pivot pins or wires, hinges, and the like). In the highly preferred embodiment of the present invention shown in FIGS. 8–12, grooves 176 are located between the sets 146–151 of electrical connectors to permit the sets to flex with respect to one another. The grooves preferably extend across the length of the opened enclosure 112, but in alternate embodiments can be shorter or interrupted as desired.

In addition to or as an alternative to the grooves 176 in the soft jackbox 110, jackbox flexure about different locations and about different axes is possible. For example, grooves that are substantially parallel to the hinge 124 can be located between electrical connectors in one or more of the sets 146, 151. As another example, an integral set of electrical connectors 114 can be notched, scored, or otherwise have weakened areas between the electrical connectors 114 to increase flexibility about axes substantially parallel to the hinge 124. In still another example, the electrical connectors 114 can each have some degree of independent movement (e.g., each electrical connector 114 having its own independent footing 161, adjacent connectors pivotably coupled or hinged to one another, etc.), thereby increasing enclosure flexibility about multiple axes in multiple orientations. One having ordinary skill in the art will appreciate that a number of other manners exist for increasing the flexibility of the enclosure 112, each one of which falls within the spirit and scope of the present invention.

Although the entire enclosure 112 of preferred soft jackbox embodiments are deformable, it should be noted that alternative embodiments of the present invention can employ enclosures having only portions that are deformable by the user for increased access to the electrical connections. In this regard, an enclosure can even have some electrical connectors that are accessible by deforming one or more portions of the enclosure and other electrical connectors that are accessible by linking or pivot mechanisms such as those described above for the hard jackbox embodiment. Also, the jackbox of either embodiment shown in FIGS. 1–7 and 8–12 can be made partially or entirely of a substantially rigid and non-deformable material covered, coated, or enclosed with a softer material, such as a resilient and deformable material. For example, the hard jackbox embodiment described above and illustrated in FIGS. 1–7 can be partially or fully covered, coated, or enclosed within a resilient and deformable material, or the soft jackbox embodiment described herein and illustrated in FIGS. 8–12 can have one or more enclosure portions that have embedded or underlying non-deformable elements. Such soft coating, covering, or enclosing material can be attached or applied to any jackbox embodiment of the present invention in any conventional manner, such as by being dipped, sprayed, laminated, attached with conventional fasteners, adhesive, cohesive, and the like. Softer (and preferably resilient and deformable) coating, covering, or enclosing material makes the jackbox 10, 110 more comfortable to wear and gives a degree of additional shock resistance to the jackbox 10, 110.

To simplify the process of connecting and disconnecting the electrical leads 116, the electrical connectors 114 can be provided with distinguishing indicia on a visible surface thereof. This indicia can take any of the forms described above with reference to the hard jackbox 10 and can be attached, applied or formed in any of the manners also described above with reference to the hard jackbox 10. However, each electrical connector 114 is most preferably molded with the indicia or has the indicia applied thereto in any conventional manner.

As an alternative to or in addition to electrical connector indicia connected, formed or applied to the electrical connectors 114, it is possible to use replaceable labels having indicia thereon to help distinguish each electrical connector 114. Examples of such labels are described above with regard to the hard jackbox 10. In yet another manner of labeling the electrical connectors 114, the enclosure 112 can be adapted to removably receive electrical connector labels. For example, and as best seen in FIG. 10, the soft jackbox 112 preferably has a number of windows 178 through the enclosure 112 adjacent to the electrical connectors 114. One or more labels (not shown) in the form of sheets or cards can be positioned behind these windows 178 so that when the jackbox 110 is opened to the position shown in FIGS. 9 and 11, at least a portion of the labels can be seen through the windows 178. The labels preferably have indicia thereon which is substantially aligned with the windows 178 and which corresponds to the adjacent electrical connectors 114. Like the labels described above with reference to the hard jackbox 10 embodiment, the use of such labels permits a user to remove and replace the labels so that the associated electrical connectors 114 can be assigned different or new indicia by the user based upon preference or application. If desired, each label can have multiple sets of indicia thereon so that a user can position one of a number of predetermined indicia sets (corresponding to one of a number of predetermined electrical connections setups, for example) in the windows 178.

The shape and arrangement of the windows 178 in the enclosure 112 is at least partially dependent upon the arrangement of the electrical connectors 114 in the jackbox 110 at least when the jackbox 110 is in its open position. As such, the shape of the labels and the position(s) of indicia thereon can have a number of different shapes dependent upon electrical connector arrangement and the shape of the enclosure 112. Any number of labels can be used (one per window 178 or one for multiple windows 178), and any number of windows 178 can be located in the enclosure 112 (one window 178 per electrical connector 114 or one window 178 for two or more electrical connectors 114). The labels can be positioned behind the windows 178 in any desired manner, such as by sliding the labels through slots (not shown) in any of the sides of the enclosure 112, by sliding the labels through pockets or sleeves on the outside of the enclosure 112 located behind the windows 178, by sliding the labels into interior pockets or sleeves located on the inside surfaces of the enclosure 112, attached thereto, or molded therein, etc.

It should be noted that the various manners described above for distinguishing electrical connectors 14, 114 from one another and for distinguishing electrical leads 16, 116 from one another can be employed for jackboxes regardless of the type of enclosure used, its manner of opening or closing, its shape or size, and the arrangement of electrical connectors 14, 114 therein.

With regard to the present invention described above and illustrated in FIGS. 1–12, it is most desirable to employ an enclosure that is fully enclosed or at least substantially fully enclosed because such an enclosure better protects the electrical connections 18, 118 against dust, spills, foreign matter, and corrosion that can be caused by these elements.

Fully enclosed or substantially fully enclosed jackboxes are also more readily adaptable to provide optional electromagnetic shielding for the electrical connections 18, 118 and the circuitry within the jackbox 10, 110. Specifically, highly preferred embodiments of the jackbox 10, 110 according to the present invention have enclosures 12, 112 that are either made from or have conventional electromagnetic interference shielding material attached thereto in any conventional manner. Such material can line the jackbox enclosure 12, 112, can surround the jackbox enclosure 12, can be impregnated, layered, molded, or cast within the walls of the enclosure 12, 112, and the like. Electromagnetic interference shielding material, its manner of operation, and methods of shielding material connection to enclosures are well known to those skilled in the art and are not therefore described further herein. Electromagnetic interference shielding material preferably surrounds as much of the electrical connectors 14, electrical leads 16, and electrical connections 18 as possible (typically determined at least in part by the shape of the enclosure 12, 112), but can be selectively positioned and employed to shield only certain portions of the jackbox 10, 110 if desired.

Highly preferred embodiments of the present invention can employ electrical connectors 14, 114 that are electromagnetically shielded in a two-conductor design. Specifically, one conductor of each electrical connector 14, 114 (e.g., the center pin 36) can carry the signals received from the patient, while another conductor of each electrical connector 14, 114 (e.g., an inner conductive lining within shroud 38) can be electrically connected to system ground, such as by dedicated wiring or circuitry to the electrical port 30 and thereby to a host grounding circuit, by electrical connection to the electromagnetic shielding material of the jackbox 10, 110 described above (itself preferably electrically connected to ground in any conventional manner), and the like. Most preferably, embodiments employing such two-conductor electrical connectors 14, 114 are used in conjunction with two-conductor electrical leads 16, 116 and electrical lead ends 40, 140. An example of such a two-conductor electrical lead 16, 116 is a coaxial cable, which has a central signal-carrying conductor surrounded by a shielding conductor. Where two-conductor electrical leads are used, one conductor of each electrical lead 16, 116 and lead end 40, 140 is electrically connected to the ground conductor of the two-conductor electrical connector 14, 114, while another conductor of each electrical lead 16, 116 and lead end 40, 140 is electrically connected to the other conductor of the two-conductor electrical connector 14, 114. Two-conductor electrical leads, their design, and their manner of connection and disconnection are well known to those skilled in the art and are not therefore described further herein. Use of shielded electrical leads 16, 116 and of a jackbox design having shielded connections 18, 118, electronics, and circuitry as described above permits the use of monitoring equipment in locations where conventional monitoring equipment cannot be used due to electromagnetic interference.

The jackbox 10, 110 of the present invention preferably can be secured in a closed position in any conventional manner. For example, the jackbox can be provided with one or more conventional clip and detent fasteners, hook and aperture fasteners, buckles, ties, hook and loop fastener strips, snaps, magnets, ties, or other well known fastening devices positioned to bridge across two adjacent portions of the enclosure 12, 112 when the jackbox 10, 110 is closed. For example, the jackbox 10 of the first preferred embodiment shown in FIGS. 1–7 preferably employs sets of resilient clip arms 80 releasably mating within suitably positioned receptacles in the base 20 of the enclosure. The clips 80 preferably have a fit within their receptacles that is tight enough to keep the enclosure 12 in a closed position but that is loose enough to be pulled apart by a user. The jackbox 110 of the second preferred embodiment shown in FIGS. 8–12 preferably employs clips 180 mating with sockets and functioning in a similar manner to that just described. If desired, one or more sets of finger detents or grips (see for example finger grips 182 on the enclosure 12 illustrated in FIG. 1) can be located on the enclosure to help the user manipulate the jackbox 10, 110 into its open and closed positions.

The fasteners 80, 180 used to releasably retain the jackboxes 10, 110 in their closed positions can also be used to connect multiple jackboxes together. Specifically, it is possible in some highly preferred embodiments of the present invention to connect fasteners from one jackbox 10, 110 to mating fasteners of another jackbox 10, 110. By way of example only, and with reference to the soft jackbox embodiment of FIGS. 8–12, two opened jackboxes 110 can be connected in facing relationship, with the clips 180 of one jackbox 110 being releasably received within the sockets of another to result in a larger jackbox providing the same advantages as the individual jackboxes 110. Any number of fasteners can be used and located in the same or different positions on mating jackboxes to accomplish such a connection or to enable even more jackboxes to be connected together. By way of example again, fasteners such as those of the soft jackbox 110 illustrated in FIGS. 8–12 can be located on the "pages" of the soft jackbox 110 so that each page mates with a page from a different soft jackbox. This pattern of connections can be extended for any number of desired jackboxes 110. End pages of such a connected structure can be left unconnected, connected to a cover, or to respective half-jackboxes, if desired. Also, jackboxes such as the highly preferred embodiment shown in FIGS. 8–12 can have multiple pages coupled side by side or end by end to connect to other jackboxes in any of the manners just described. Similar connectivity is possible between any of the other jackbox types described herein, limited only by the shape of the jackbox, its manner of opening, and the positions it can take when opened.

A number of conventional manners also exist for releasably coupling multiple jackboxes together, such as via mating fasteners on outer surfaces of the jackboxes and/or mating jackbox shapes, and the like. Fasteners that can be used include without limitation mating clips, hook and loop fastener material, mating male and female connectors (e.g., one or more mating pins and sockets having a light interference fit, threaded fasteners mating with threaded sockets, etc.), magnets, ties, and the like. Jackbox mating shapes (most preferably, mating shapes of their enclosures) include without limitation dovetail joints, mating protrusions and receptacles, and the like. Any of these fasteners and fastening shapes can be used not only to releasably couple adjacent jackboxes, but also to couple jackboxes to a wearer's belt, clothing, harness, holster, or other worn item having mating fasteners or fastening shapes and/or to couple jackboxes to related equipment such as a signal amplifier, transmitter, or other device also having mating fasteners or fastening shapes. Any fastener or fastener shape capable of releasably connecting the jackbox of the present invention to another jackbox, to an item worn by the wearer, and/or to other monitoring equipment can be used and falls within the spirit and scope of the present invention.

The embodiments described above and illustrated in the figures are presented by way of example only and are not intended as a limitation upon the concepts and principles of the present invention. As such, it will be appreciated by one having ordinary skill in the art that various changes in the elements and their configuration and arrangement are possible without departing from the spirit and scope of the present invention as set forth in the appended claims.

For example, although the clamshell and book-type jackbox enclosures are preferred for the jackbox embodiments described above and illustrated in the figures, a number of other jackbox enclosure shapes can be employed in the present invention. Possible alternative shapes of the enclosure include disc, bar, cube, oval and polygonal shapes. One having ordinary skill in the art will appreciate that each enclosure type can open and close in a number of different manners, whether by a portion of the enclosure coupled to move relative to other portions of the enclosure (e.g., top and bottom halves, front and rear sections, and the like) or by a panel, door or wall slidably, pivotably, or detachably coupled to the enclosure for user access to the interior thereof. Also, alternative embodiments of the present invention can have multiple enclosure chambers 28, 128 or sections capable of being opened by movement of one or more enclosure portions. By way of example only, one part of the enclosure can be closed over multiple compartments defined by another part of the enclosure, the book or clamshell-style enclosures 12, 112 of the preferred embodiments above can have multiple "pages" or levels arranged, oriented, and accessible in similar manners to the jackbox portions described above—each having a number of electrical connectors 14, 114 therein, or the jackbox enclosure can have multiple doors or enclosure portions movable to access different electrical connector locations within the enclosure, etc. Each of the various enclosure types can be made of resilient substantially non-deformable material such as the hard jackbox of FIGS. 1–7 or of semi-deformable or deformable material such as the soft jackbox of FIGS. 8–12. Also, each enclosure type can employ a pivot mechanism as described above to transfer enclosure opening and closing movement to movement of one or more electrical connectors 14, 114 inside the enclosure, or can rely upon enclosure flexibility to increase user access to one or more of the electrical connectors 14, 114.

Figure 13:
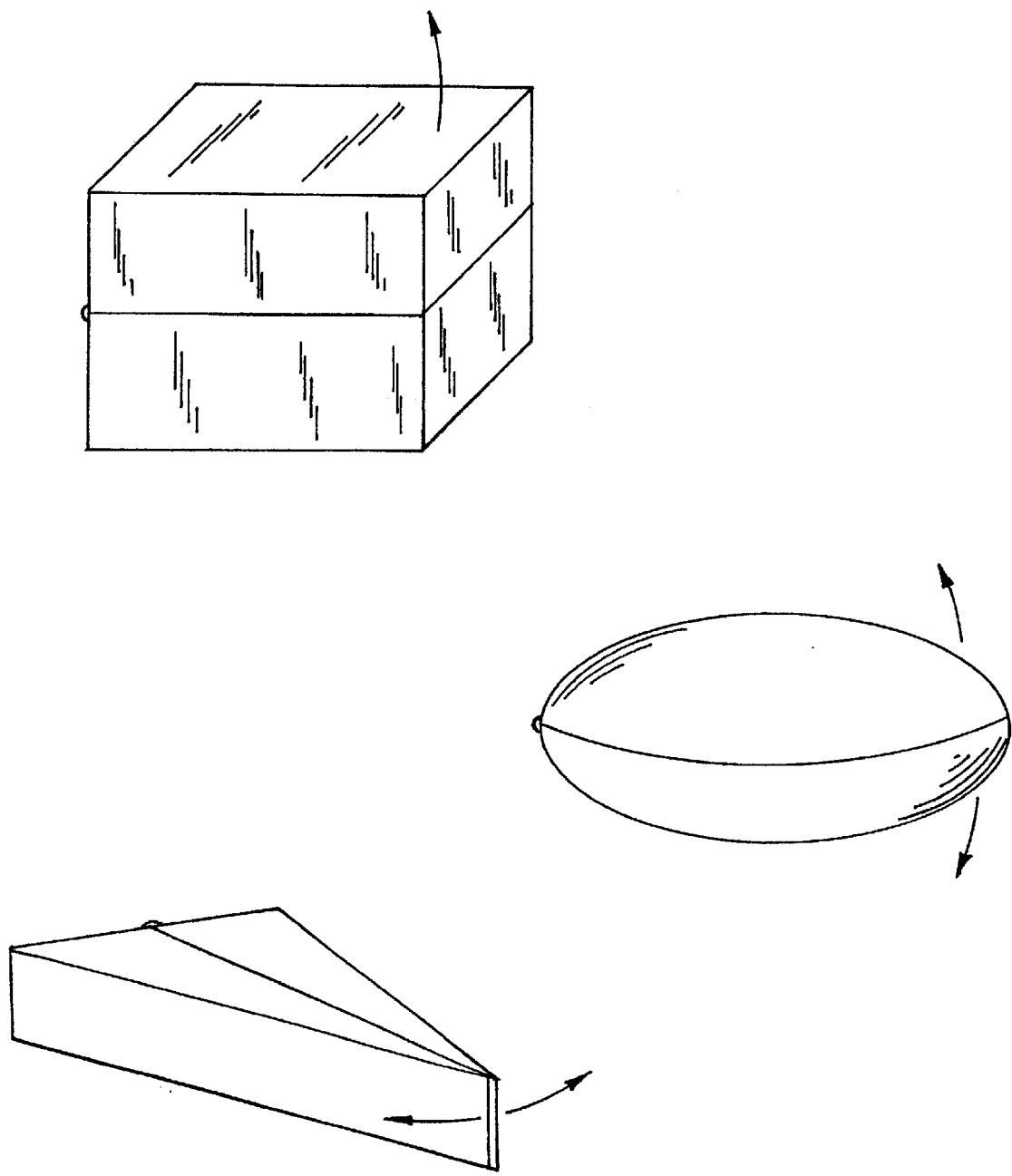
FIG. 13 is a number of alternative jackbox shapes according to alternative preferred embodiments of the present invention.

Still other alternative embodiments of the present invention can have enclosures that only surround, cover, or otherwise shield portions of the jackbox. For example, such enclosures can have portions shielding only the electrical connections 14, 114 on one or more sides, shielding only the edges of the jackbox 10, 110, shielding only the flex circuits 34, 134, shielding only some of the electrical connections 18, etc. The enclosure can shield any amount of the jackbox in any location as desired. Also, it is possible to employ enclosures that have limited or no access to areas within the enclosure. For example, one preferred enclosure according to the present invention is not user-openable and is made from resilient and deformable material such as is used in the soft jackbox 110 described above. As also described herein, the enclosure can be any shape and size desired (including without limitation cube, brick, bar, round, oval, polygonal, or other shapes ranging from simple to complex and unusual). A number of alternative jackbox shapes are shown by way of example only in FIG. 13. It should be noted that the shapes illustrated in FIG. 13 can be those of the enclosure or of the jackbox itself (having an enclosure or not). The enclosure is formed in any of the manners described above with reference to the enclosure 112 of the soft jackbox embodiments. The electrical connectors 14, 114 in this type of enclosure are at least partially embedded in the enclosure (flush with, protruding slightly from, or recessed slightly with respect to one or more exterior surfaces of the enclosure) and are accessible for connection and disconnection from outside of the enclosure. Preferably, the electrical connectors 14, 114 are nested in sets or other groups as described above, but can be arranged in any other manner desired. Although this preferred embodiment is not openable and closable to fully enclose the electrical connectors 14, 114 and to orient the electrical connectors 14, 114 for the purposes described above, the resilient and deformable material significantly reduces the chances of jackbox damage due to dropping, impact, pressure, and other abuse, is more comfortable to wear than conventional jackboxes due to its ability to contour to the wearer's body and to absorb compressive forces, and can still provide a limited amount of electrical connector 14, 114 manipulation due to the deformable material used to make the enclosure.

It is even possible to practice the present invention without an enclosure at all. In the hard jackbox embodiment described above, for example, the enclosure 10, can be replaced by a resilient frame (e.g., made from plastic, metal, or composite bars or rods connected together in a conventional manner) connected to the sets 46, 48, 50, 52 of electrical connectors 14 and to the linking mechanism 62 in the same or similar manner as described for the enclosure 10. In the soft jackbox embodiment, for example, the enclosure 110 can also be replaced by a deformable or semi-deformable frame (e.g., made from resilient flexible plastic or other synthetic material, a plurality of links pivotably coupled together, etc.) connected to the sets 146–151 of electrical connectors 114 or their footings 161 in any conventional manner. The frame in each such embodiment can be extended to connect to elements such as electrical ports 30, 130, jackbox identifiers 44, 144, retaining elements 60, 160, and the like as desired.

It should be noted that the electrical connectors 14, 114 in the various embodiments of the present invention can be arranged in any manner desired within the jackbox 10, 110. Although sets of electrical connectors 14, 114 lined in rows are most preferred, such an arrangement is not required. The electrical connectors 14, 114 can be mounted in the jackbox in pods or small bundles, can be mounted to point in a number of different directions, or can be individually mounted in desired locations within the jackbox. When arranged in sets, any number of sets can be used in the jackbox 10, 110 in any desired pattern. Regardless of the arrangement selected, however, it is preferred (though not required) to employ the nesting and offset features described above for space conservation, lower electrical lead stress, and better electrical lead and connector organization. As used herein and in the appended claims, the terms "set" refers to two or more of the elements adjacent to one another, and does not indicate or imply any particular relative position of such elements (i.e., side by side, front to back, top and bottom, pointed in the same direction or in different directions and the like).

With regard to the electrical connector arrangements just described, not all electrical connectors 14, 114 need to be located within the enclosure 12, 112 in its closed position. One or more electrical connectors 14, 114 can be exteriorly mounted on the jackbox 10, 110 or be accessible from outside of the closed enclosure, if desired. Also, not all electrical connectors 14, 114 need to be connected to electrical leads 16, 116 carrying the signals representative of the same physiological parameter of the patient (such as EEG signals). Instead, one or more electrical connectors 14, 114 can be employed for receiving electrical leads carrying signals representative of a variety of other parameters, including without limitation pulse oximetry signals, electrocardiographic (EKG) signals, blood pressure signals, etc. Preferably, where one or more electrical connectors 14, 114 are used for different signal types than the others, they are colored, marked, shaped, provided with indicia, or otherwise present some different appearance and/or are set apart a distance (inside or outside of the enclosure 12, 112) from the other electrical connectors 14, 114 for easy user identification.

In the following claims, it should be noted that reference to an element or to a claimed number of elements does not preclude the existence of more such elements in the device claimed. Also, when one element is said to be "coupled" to another, this does not necessarily mean that one element is fastened, secured, or otherwise attached to another element. Instead, the term "coupled" means that one element is either connected directly or indirectly to another element or is in mechanical or electrical (including wireless) communication with another element.

We claim:

1. A jackbox for releasably coupling a plurality of electrical leads to associated equipment, the plurality of electrical leads connectable to a patient and to the jackbox for carrying signals corresponding to at least one physiological parameter of the patient, the jackbox comprising:

an enclosure having an open position and a closed position; and a plurality of electrical connectors connectable to at least some of the plurality of electrical leads carrying the signals corresponding to the at least one physiological parameter of the patient, the plurality of electrical connectors located inside the enclosure from which the plurality of electrical leads extend to the patient, the plurality of electrical leads extending from the patient to the jackbox being disconnectable from the plurality of electrical connectors when the enclosure is in its open position and resistant to disconnection when the enclosure is in its closed position, the plurality of electrical connectors being accessible when the enclosure is in its open position and being substantially inaccessible when the enclosure is in its closed position.

2. The jackbox as claimed in claim 1, wherein the retaining element at least partially defines at least one aperture through which the plurality of electrical leads run when connected to the plurality of electrical connectors and when the enclosure is in its closed position.

3. The jackbox as claimed in claim 1, wherein the enclosure includes shielding material to shield the plurality of electrical connectors and the plurality of leads from electromagnetic interference.

4. The jackbox as claimed in claim 1, wherein the enclosure has a first body portion and a second body portion rotatably coupled thereto for opening and closing the enclosure, the jackbox further comprising a pair of linking elements coupled to the plurality of electrical connectors and coupled between the first and second body portions for movement between a position in which the linking elements are adjacent one another and a position in which the linking elements are oriented at an angle with respect to one another.

5. The jackbox as claimed in claim 1, wherein each electrical connector is mounted for independent pivotal movement within the enclosure.

6. The jackbox as claimed in claim 1, wherein the enclosure has a first body portion and a second body portion, the first and second body portions coupled together in a clamshell form defining a cavity therebetween when the enclosure is in its closed position.

7. The jackbox as claimed in claim 6, further comprising a retaining element coupled to the enclosure and shaped to at least partially surround the plurality of electrical leads when the enclosure is in its closed position, the retaining element substantially blocking movement of the plurality of electrical leads out of the enclosure in its closed position.

8. The jackbox as claimed in claim 1, further comprising a retaining element coupled to the enclosure, the retaining element positioned to obstruct movement of the plurality of electrical leads away from connection with the plurality of electrical connectors.

9. The jackbox as claimed in claim 8, wherein the retaining element clamps the plurality of electrical leads against movement out of the enclosure in its closed position.

10. The jackbox as claimed in claim 1, wherein the plurality of electrical connectors are arranged in sets of side-by-side and substantially parallel electrical connectors.

11. The jackbox as claimed in claim 10, wherein at least one of the sets of electrical connectors is blocked from disconnection by interference with another set of electrical connectors when the enclosure is in its closed position.

12. The jackbox as claimed in claim 10, wherein at least two of the sets of electrical connectors are in a nested relationship with one another when the enclosure is in its closed position.

13. The jackbox as claimed in claim 1, wherein the enclosure has a first body portion and a second body portion rotatably coupled thereto for opening and closing the enclosure, the jackbox further comprising at least one linking element coupled to the electrical connectors and to the enclosure for movement in response to relative movement between the first and second body portions.

14. The jackbox as claimed in claim 13, wherein the electrical connectors are coupled to the enclosure and to the at least one linking element.

15. The jackbox as claimed in claim 13, wherein the plurality of electrical connectors are arranged in sets of side-by-side and substantially parallel electrical connectors, at least one end of each set being connected to a linking element.

16. The jackbox as claimed in claim 13, further comprising a plurality of labels coupled to the plurality of electrical leads, each of the plurality of labels having indicia thereon associated with indicia of a corresponding electrical connector.

17. The jackbox as claimed in claim 13, wherein the plurality of labels are a plurality of sleeves each adapted to fit around an electrical lead.

18. The jackbox as claimed in claim 13, further comprising a label receptacle on an exterior surface of the enclosure, the label receptacle adapted to receive a label therein.

19. The jackbox as claimed in claim 13, further comprising a wireless transmitter coupled to the plurality of electrical connectors for transmitting the signals from the jackbox to a signal receiver.

20. The jackbox as claimed in claim 13, wherein each linking element is coupled between the first and second body portions.

21. The jackbox as claimed in claim 20, wherein the each linking element is pivotably coupled at one end to the first body portion and at another end to the second body portion.

22. A method of releasably coupling a plurality of electrical leads carrying signals corresponding to at least one physiological parameter of a patient to associated equipment, the method comprising the steps of:

opening an enclosure to expose a plurality of electrical connectors mounted therein;

releasably connecting a first end of each one of the plurality of electrical leads carrying the signals corresponding to the at least one physiological parameter of the patient to each one of the plurality of electrical connectors;

feeding the plurality of electrical leads carrying the signals corresponding to the at least one physiological parameter of the patient out of at least one aperture defined in the enclosure;

closing the enclosure to substantially enclose the plurality of electrical connectors and secure the plurality of electrical leads carrying the signals corresponding to the at least one physiological parameter of the patient against disconnection by pulling forces exerted upon the leads; and releasably attaching a second end of the plurality of electrical leads to the patient to acquire the signals corresponding to the at least one physiological parameter of the patient.

23. The method as claimed in claim 22, wherein the enclosure opens and closes in the manner of a clamshell.

24. The method as claimed in claim 22, wherein the securing step includes clamping the plurality of electrical leads against a retaining element coupled to the enclosure.

25. The method as claimed in claim 22, wherein the securing step includes clamping the plurality of electrical leads between retaining elements coupled to the enclosure.

26. The method as claimed in claim 22, wherein the securing step includes moving a number of the electrical connectors to a position between a number of the leads and the aperture, the number of electrical connectors blocking the number of leads against disconnection from their associated electrical connectors.

27. The method as claimed in claim 22, wherein the electrical connectors are arranged in sets of electrical connectors, the method further comprising the step of nesting one set of electrical connectors within another set during the closing step.

28. The method as claimed in claim 22, further comprising the step of shielding the plurality of electrical connectors and the plurality of electrical leads located in the enclosure against electromagnetic interference.

29. The method as claimed in claim 22, wherein the aperture is at least partially defined by and between two portions of the enclosure movable relative to one another to open and close the enclosure.

30. The method as claimed in claim 22, wherein the releasably connecting step includes matching each electrical lead to a corresponding electrical connector via indicia upon a band on each electrical lead corresponding to indicia associated with each electrical connector.

31. The method as claimed in claim 22, further comprising the step of pivoting at least some of the electrical connectors in the enclosure to desired positions.

32. The method as claimed in claim 22, further comprising the step of pivoting at least one electrical connector independently of the other electrical connectors.

33. The method as claimed in claim 22, further comprising the step of pivoting the plurality of electrical connectors in response to the opening and closing steps.

34. The method as claimed in claim 22, further comprising the step of pivoting separate sets of the electrical connectors in response to the opening and closing steps.

35. The method as claimed in claim 22, wherein the plurality of electrical connectors are arranged in at least two sets of electrical connectors connected to a respective pair of linking elements in the enclosure, and wherein the opening and closing steps include pivoting one linking element with respect to another linking element to change a distance between the sets of electrical connectors.

36. The method as claimed in claim 22, further comprising the step of transmitting the signals via a wireless connection to a signal receiver.

37. The method as claimed in claim 22, wherein the securing step includes blocking the plurality of electrical leads against removal from the enclosure by a retaining element coupled to the enclosure and located adjacent to the plurality of electrical leads when the enclosure is closed.

38. The method as claimed in claim 37, wherein the retaining element at least partially defines the aperture.

39. A jackbox for releasably coupling a plurality of electrical leads to associated equipment, the leads carrying signals corresponding to at least one physiological parameter of a patient, the jackbox comprising:
an enclosure having a body portion, the enclosure being movable between an open position and a closed position; and
a plurality of electrical connectors mounted to the body portion within the enclosure and adapted for releasable connection to the plurality of electrical leads carrying the signals, the plurality of electrical connectors mounted for relative motion with respect to the body portion in response to movement of the enclosure between its open and closed positions.

40. The jackbox as claimed in claim 39, wherein at least some of the plurality of electrical connectors are mounted in the enclosure for independent pivotal movement.

41. The jackbox as claimed in claim 39, wherein the enclosure is openable and closable in clamshell form.

42. The jackbox as claimed in claim 39, wherein the body portion is a first body portion, the jackbox further comprising:
a second body portion movable with respect to the first body portion in clamshell form to open and close the enclosure, wherein some of the plurality of electrical connectors are mounted adjacent to the first body portion in the open and closed positions of the enclosure, and wherein some of the plurality of electrical connectors are mounted adjacent to the second body portion in the open and closed positions of the enclosure.

43. The jackbox as claimed in claim 39, further comprising a retaining element coupled to the enclosure and in contact with the plurality of electrical leads at least when the enclosure is in its closed position, the retaining element positioned to obstruct removal of the plurality of electrical leads from the enclosure when in its closed position.

44. The jackbox as claimed in claim 39, wherein the body portion is a first body portion, the jackbox further comprising:
a second body portion movable with respect to the first body portion to open and close the enclosure, and
a hinge mechanism having a linking element coupled at a first point to the first body portion and at a second point to at least some of the plurality of electrical connectors defining a first set of electrical connectors.

45. The jackbox as claimed in claim 44, wherein the linking element is mounted for pivotal movement at the first and second points.

46. The jackbox as claimed in claim 45, wherein the first set of electrical connectors is coupled to the second body portion.

47. The jackbox as claimed in claim 46, wherein the first set of electrical connectors is mounted for pivotal movement to the second body portion.

48. The jackbox as claimed in claim 44, wherein the first set of electrical connectors is coupled to the second body portion.

49. The jackbox as claimed in claim 48, wherein the first set of electrical connectors is pivotably coupled to the second body portion.

50. The jackbox as claimed in claim 44, wherein the linking element is a first linking element and wherein the hinge mechanism has a second linking element mounted for pivotal movement with respect to the first linking element, the second linking element coupled to another plurality of electrical connectors defining a second set of electrical connectors.

51. The jackbox as claimed in claim 50, wherein the first and second linking elements are pivotable into a first position in which the first and second sets of electrical connectors are adjacent to one another and a second position in which the first and second sets of electrical connectors are spread a distance apart from one another, the first and second positions of the sets of electrical connectors corresponding to the closed and open positions of the enclosure, respectively.

52. The jackbox as claimed in claim 51, wherein the first and second sets of electrical connectors are nested within one another when the first and second sets are in the first position.

53. The jackbox as claimed in claim 44, further comprising a second set of electrical connectors coupled at a third point to the linking element.

54. The jackbox as claimed in claim 53, wherein the first and second sets of electrical connectors are positioned in substantially parallel rows within the enclosure.

55. The jackbox as claimed in claim 39, wherein the plurality of electrical connectors includes first and second sets of electrical connectors for releasable connection to first and second sets of the plurality of electrical leads, respectively, and wherein the first set of electrical connectors is positioned to limit movement of the second set of electrical leads when coupled to the second set of electrical connectors in the closed position of the enclosure.

56. The jackbox as claimed in claim 55, wherein the first set of electrical connectors is at least partially nested within the second set of electrical leads.

57. The jackbox as claimed in claim 39, wherein the plurality of electrical connectors include first and second sets of electrical connectors movable relative to one another in response to movement of the enclosure between its open and closed positions, the first and second sets of electrical connectors adapted for releasable connection to first and second pluralities of leads, respectively.

58. The jackbox as claimed in claim 57, wherein the first and second sets of electrical leads are nested together when the enclosure is in its closed position.

59. A method of releasably coupling a plurality of electrical leads carrying signals corresponding to at least one physiological parameter of a patient to a device, the method comprising the steps of:

opening an enclosure within which a plurality of electrical connectors are mounted, the enclosure having a body portion to which the plurality of electrical connectors are mounted;

moving the plurality of electrical connectors with respect to the body portion to provide greater accessibility thereto in response to and substantially simultaneously with the opening step; and releasably connecting the plurality of electrical leads carrying the signals to the plurality of electrical connectors.

60. The method as claimed in claim 59, further comprising the steps of:

closing the enclosure; and moving the plurality of electrical connectors in response to and substantially simultaneously with the closing step.

61. The method as claimed in claim 59, wherein the moving step comprises pivoting the plurality of electrical connectors.

62. The method as claimed in claim 59, wherein the plurality of electrical connectors include at least two sets of electrical connectors, and wherein the moving step comprises separately pivoting the sets of electrical connectors.

63. The method as claimed in claim 59, wherein the moving step includes moving at least one linking element pivotably coupled to the enclosure and to the plurality of electrical connectors.

64. The method as claimed in claim 59, including the step of independently pivoting one of the plurality of electrical connectors.

65. The method as claimed in claim 59, further comprising the steps of:

closing the enclosure; and preventing disconnection of the plurality of electrical leads by a retaining element adjacent to the plurality of electrical leads.

66. The method as claimed in claim 59, further comprising the steps of:

closing the enclosure; and preventing disconnection of the plurality of electrical leads by moving a retaining element to a position adjacent to the plurality of electrical leads during the closing step.

67. The method as claimed in claim 59, further comprising the steps of:

closing the enclosure; and preventing electrical lead disconnection by moving a set of the electrical connectors during the closing step into retaining positions adjacent to a set of the electrical leads, the set of electrical connectors in their retaining positions preventing removal of the set of electrical leads from their corresponding electrical connectors.

68. The method as claimed in claim 59, further comprising the steps of:

closing the enclosure; and nesting a first set of the plurality of electrical leads into a second set of the plurality of electrical leads during the closing step.

69. A jackbox wearable by a patient for releasably coupling a plurality of electrical leads to associated equipment, the leads carrying signals corresponding to at least one physiological parameter of the patient, the jackbox comprising:

an enclosure made at least partially of resilient deformable material and capable of contouring under pressure to the patient's body; and a plurality of electrical connectors mounted within the resilient deformable enclosure and adapted for releasable connection to the plurality of electrical leads carrying the signals.

70. The jackbox as claimed in claim 69, wherein the enclosure has:

a closed position in which the plurality of electrical connectors are at least partially enclosed;

an open position providing increased user access to the plurality of electrical connectors; and at least one lead outlet through which the plurality of leads pass from outside of the enclosure to connect to the plurality of electrical connectors inside the enclosure.

71. The jackbox as claimed in claim 69, wherein the enclosure comprises a molded thermoplastic elastomer.

72. The jackbox as claimed in claim 69, wherein the enclosure is shielded against electromagnetic interference.

73. The jackbox as claimed in claim 69, further comprising a flex circuit coupled to the plurality of electrical connectors, the flex circuit flexible and capable of contouring with the enclosure under pressure.

74. The jackbox as claimed in claim 69, further comprising a retaining element positioned to obstruct removal of the plurality of electrical leads from their associated electrical connectors when the enclosure is in a closed position.

75. The jackbox as claimed in claim 69, wherein a set of the plurality of electrical connectors are positioned in the enclosure to obstruct removal of a set of electrical leads when the enclosure is in a closed position.

76. The jackbox as claimed in claim 69 for being worn upon the waist of the patient, wherein the plurality of electrical connectors and plurality of electrical leads are oriented substantially vertically when the jackbox is worn by the patient.

77. The jackbox as claimed in claim 69 for being worn upon the patient's body, wherein the plurality of electrical connectors and plurality of electrical leads are oriented substantially parallel to the patient's body when the jackbox is worn thereon.

78. The jackbox as claimed in claim 69, further comprising:
    at least one window defined in the enclosure; and
    at least one label positionable adjacent to the at least one window, the at least one label having indicia thereon corresponding to electrical connectors located adjacent to the at least one window.

79. The jackbox as claimed in claim 69, wherein at least some of the plurality of electrical connectors are mounted for pivotal rotation in the enclosure.

80. The jackbox as claimed in claim 69, wherein at least some of the plurality of electrical connectors are molded in place within the enclosure.

81. The jackbox as claimed in claim 69, wherein the enclosure includes:
    a first body portion; and
    a second body portion movable with respect to the first body portion to open and close the enclosure.

82. The jackbox as claimed in claim 81, wherein the first and second body portions are movable in clamshell form to open and close the enclosure.

83. A method of coupling a plurality of electrical leads carrying signals corresponding to at least one physiological parameter of a patient to a device, the method comprising the steps of:
    opening an enclosure having a plurality of electrical connectors mounted therein;
    connecting the plurality of leads carrying the signals to the plurality of electrical connectors;
    closing the enclosure with the electrical leads carrying the signals extending from an aperture defined in the enclosure;
    securing the enclosure upon a part of the user; and
    resiliently conforming the enclosure to the part of the user in response to force exerted upon the enclosure.

84. The method as claimed in claim 83, further comprising the step of pivoting at least one of the electrical connectors for increased connecting access thereto.

85. The method as claimed in claim 83, further comprising the step of shielding the plurality of electrical connectors and the plurality of leads from electromagnetic interference.

86. The method as claimed in claim 83, further comprising the step of retaining a set of the electrical leads within the enclosure by positioning at least some of the electrical connectors between the set of electrical leads and the aperture.

87. The method as claimed in claim 83, wherein the securing step includes orienting the enclosure so that the plurality of electrical connectors and the plurality of electrical leads are substantially parallel to the patient.

88. The method as claimed in claim 83, further comprising the step of nesting a first set of the electrical leads into a second set of the electrical leads during the closing step.

89. The method as claimed in claim 83, further comprising the step of nesting a first set of the electrical connectors into a second set of the electrical connectors during the closing step.

90. The method as claimed in claim 83, further comprising the step of nesting a set of the electrical connectors into a set of the electrical leads during the closing step.

91. The method as claimed in claim 83, further comprising the step of conforming a flexible circuit to the part of the patient in response to force exerted upon the enclosure, the flexible circuit coupled to plurality of electrical connectors.

92. The method as claimed in claim 83, further comprising the step of securing the plurality of leads against disconnection by a retaining element of the enclosure.

93. The method as claimed in claim 92, wherein the step of securing the plurality of leads includes moving the retaining element into contact with the plurality of leads during the closing step.

94. The method as claimed in claim 92, wherein the step of securing the plurality of leads includes moving the retaining element to a position between the plurality of electrical connectors and the aperture.

95. A jackbox for coupling a plurality of electrical leads to associated equipment, the leads carrying signals corresponding to at least one physiological parameter of a patient, the jackbox comprising:
    a jackbox body consisting of resilient deformable material callable of conforming to the patient's body; and
    a plurality of electrical connectors at least partially embedded in the resilient deformable material and adapted for releasable connection to the plurality of electrical leads carrying the signals corresponding to the at least one physiological parameter of the-patient.

96. A method of manufacturing a jackbox for coupling a plurality of electrical leads carrying signals corresponding to at least one physiological parameter of a patient to a device, the method comprising the steps of:
    forming a body of deformable and resilient material capable of conforming to the patient's body; and
    at least partially embedding and securing a plurality of electrical connectors within the body, the electrical connectors adapted for releasable connection to the plurality of electrical leads carrying the signals corresponding to the at least one physiological parameter of the patient.

97. A jackbox for coupling a plurality of electrical leads to associated equipment, the plurality of electrical leads connectable to a patient and to the jackbox for carrying signals corresponding to at least one physiological parameter of the patient, the jackbox comprising:
    a first body portion and a second body portion coupled together in clamshell form and movable between open and closed positions, the first and second body portions defining in the closed position an enclosure and at least one lip opening therebetween, the at least one lip opening extending substantially from the enclosure to an area outside of the jackbox; and
    a plurality of electrical connectors mounted within the enclosure for receiving the signals corresponding to the at least one physiological parameter of the patient from the plurality of electrical leads, the plurality of electrical connectors releasably connectable to the plurality of electrical leads carrying the signals corresponding to the at least one physiological parameter of the patient, the plurality of electrical leads extending from the patient to the plurality of electrical connectors in the enclosure via the at least one lip opening when the first and second body portions are in their closed position.

98. A method of manufacturing a jackbox for coupling a plurality of electrical leads carrying signals corresponding to at least one physiological parameter of a patient to a device, the method comprising the steps of:
    pivotably coupling a first body portion to a second body portion in clamshell form, the first and second body portions having an enclosure defined therebetween; and
    mounting a plurality of electrical connectors within the enclosure for receiving physiological signals from the patient, the electrical connectors releasably connectable to the plurality of electrical leads carrying the signals corresponding to the at least one physiological parameter of the patient.

99. A jackbox for coupling electrical leads to associated equipment, the leads carrying signals corresponding to at least one physiological parameter of a patient, the jackbox comprising:
   an electrical connector adapted for releasable connection to an electrical lead, the electrical connector being pivotable about a first pivot point and a second pivot point;
   a linking element coupled to the electrical connector at the first pivot point; and
   the electrical connector secured against translation in the jackbox at the second pivot point, substantially translational movement of the linking element thereby causing substantially pivotal motion of the electrical connector about the second pivot point.

100. The jackbox as claimed in claim 99, wherein the linking element has a hinge permitting relative motion of different ends of the linking element.

101. The jackbox as claimed in claim 99, wherein the electrical connector is one of a battery of electrical connectors pivotably coupled to the linking element at the second pivot point, the battery of electrical connectors being substantially arranged in a plane within the enclosure.

102. The jackbox as claimed in claim 99, further comprising an enclosure within which the electrical connector and the linking element are mounted.

103. The jackbox as claimed in claim 102, wherein the enclosure includes first and second portions movable relative to one another to open and close the enclosure.

104. The jackbox as claimed in claim 103, wherein the linking element is coupled to the first and second portions of the enclosure for transferring relative motion between the first and second portions of the enclosure to motion of the linking element and the electrical connector.

105. The jackbox as claimed in claim 103, wherein the linking element has first and second ends coupled to the first and second portions of the enclosure for transferring relative motion between the first and second portions of the enclosure to motion of the linking element, the linking element having a live hinge between its first and second ends permitting relative motion of the first and second ends of the linking element.

106. The jackbox as claimed in claim 99, wherein the linking element is a first linking element, the jackbox further comprising:
   a second electrical connector adapted for releasable connection to another electrical lead, the second electrical connector being pivotable about a third pivot point and a fourth pivot point; and
   a second linking element coupled to the second electrical connector at the third pivot point and coupled to the first linking element.

107. The jackbox as claimed in claim 106, wherein the first and second linking elements are pivotable from a first position in which the first and second electrical connectors are located a distance apart to a second position in which the first and second electrical connectors are located adjacent to one another.

108. The jackbox as claimed in claim 106, further comprising an enclosure within which the electrical connectors and the linking elements are mounted.

109. The jackbox as claimed in claim 108, wherein the enclosure includes first and second portions movable relative to one another to open and close the enclosure.

110. The jackbox as claimed in claim 109, wherein the first linking element is coupled to the first and second portions of the enclosure for transferring relative motion between the first and second portions of the enclosure to motion of the first linking element and the first electrical connector, and wherein the second linking element is coupled to the second portion of the enclosure for transferring relative motion between the first and second portions of the enclosure to motion of the second linking element and the second electrical connector.

111. The jackbox as claimed in claim 101, wherein the battery of electrical connectors is a first battery of electrical connectors, the jackbox further comprising a second battery of electrical connectors pivotably coupled to the linking element at a third pivot point and secured against translation in the jackbox at a fourth pivot point, the second battery of electrical connectors being substantially arranged in a plane within the enclosure.

112. The jackbox as claimed in claim 111, wherein the first and second batteries of electrical connectors are pivotable to respective positions in which the electrical leads connected to the first battery of electrical connectors nest within the second battery of electrical connectors.

113. The jackbox as claimed in claim 99, wherein the electrical connector is pivotable by movement of the linking element into a position in which the electrical lead is obstructed from disconnection from the electrical connector.

114. The jackbox as claimed in claim 113, wherein the electrical lead is obstructed from disconnection in the position of the electrical connector by interference with a retaining element.

115. The jackbox as claimed in claim 113, wherein the electrical lead is obstructed from disconnection in the position of the electrical connector by interference with another electrical connector.

116. A method of coupling an electrical lead carrying signals corresponding to a physiological parameter of a patient to a jackbox, the method comprising the steps of:
   providing at least one linking element mounted within the jackbox;
   opening the jackbox;
   pivoting an electrical connector within the jackbox from a first position to a second position about a first pivot point on the at least one linking element in response to and substantially simultaneously with the opening step;
   releasably coupling the electrical lead carrying the signals to the electrical connector;
   closing the jackbox; and
   pivoting the electrical connector about the first pivot point toward the first position in response to and substantially simultaneously with the closing step.

117. The method as claimed in claim 116, further comprising the step of shielding the electrical connector and the electrical lead from electromagnetic interference.

118. The method as claimed in claim 116, wherein the electrical connector is a first electrical connector and wherein the electrical lead is a first electrical lead, the method further comprising the steps of:
   providing a second electrical connector within the jackbox;
   releasably coupling a second electrical lead to the second electrical connector;
   wherein the second electrical connector is positioned adjacent to the first electrical lead when the jackbox is closed, and prevents removal of the first electrical lead from the first electrical connector when the jackbox is closed.

119. The method as claimed in claim 116, wherein the electrical connector is a first electrical connector and wherein the electrical lead is a first electrical lead, the method further comprising the steps of:
provide a second electrical connector within the jackbox;
releasably coupling a second electrical lead to the second electrical connector;
wherein the second electrical lead is positioned adjacent to the first electrical lead when the jackbox is closed, and prevents removal of the first electrical lead from the first electrical connector when the jackbox is closed.

120. The method as claimed in claim 116, further comprising the step of moving a retaining element to a position adjacent to the electrical lead during the closing step, the retaining element preventing removal of the electrical lead from the electrical connector when the jackbox is closed.

121. The method as claimed in claim 116, further comprising the step of pivoting the electrical connector about the first pivot point after the opening step and before the closing step.

122. The method as claimed in claim 116 for connecting a plurality of electrical leads to a plurality of electrical connectors, wherein the step of pivoting the electrical connector from the first position to the second position includes pivoting a first set of electrical connectors from the first position to the second position.

123. The method as claimed in claim 122, further comprising the step of pivoting a second set of electrical connectors within the jackbox from a third position to a fourth position about a second pivot point on the at least one linking element in response to and substantially simultaneously with the opening step.

124. The method as claimed in claim 123, further comprising the step of nesting leads running to the first set of electrical connectors within the second set of electrical connectors during the closing step.

125. The method as claimed in claim 123, further comprising the step of nesting the first set of electrical connectors within the second set of electrical connectors during the closing step.

126. The method as claimed in claim 123, further comprising the step of nesting leads running to the first set of electrical connectors within leads running to the second set of electrical connectors during the closing step.

127. The method as claimed in claim 122, wherein the at least one linking element is a first linking element, the method further comprising the step of pivoting a second set of electrical connectors within the jackbox from a third position to a fourth position about a second pivot point on a second linking element in response to and substantially simultaneously with the opening step.

128. The method as claimed in claim 127, wherein the first and second linking elements are rotatable with respect to one another to bring the first and second sets of electrical connectors into and out of a position adjacent to one another.

129. The method as claimed in claim 128, further comprising the step of nesting leads running to the first set of electrical connectors within the second set of electrical connectors during the closing step.

130. The method as claimed in claim 128, further comprising the step of nesting the first set of electrical connectors within the second set of electrical connectors during the closing step.

131. The method as claimed in claim 128, further comprising the step of nesting leads running to the first set of electrical connectors within leads running to the second set of electrical connectors during the closing step.

132. The method as claimed in claim 116, further comprising the step of pivoting one portion of the at least one linking element about another portion during the opening and closing steps.

133. The method as claimed in claim 132, wherein the linking element portions are pivotable with respect to one another about a live hinge.

134. The method as claimed in claim 132, wherein the linking element portions are coupled together by a hinge.

135. A jackbox for coupling a plurality of electrical leads to associated equipment, the leads carrying signals corresponding to at least one physiological parameter of a patient, the jackbox comprising:
a first plurality of electrical connectors to which a first set of electrical leads are releasably connectable to define a first layer of electrical connections;
a second plurality of electrical connectors to which a second set of electrical leads are releasably connectable to define a second layer of electrical connections;
the first layer of electrical connections nested at least partially within the second layer of electrical connections.

136. The jackbox as claimed in claim 135, wherein the first and second layers lie substantially in respective first and second substantially parallel planes.

137. The jackbox as claimed in claim 135, wherein the first and second layers lie substantially in respective first and second planes converging in a direction leading away from the electrical connectors along the electrical leads.

138. The jackbox as claimed in claim 135, wherein the first and second layers of electrical connections are staggered so that the first layer partially overlies the second layer.

139. The jackbox as claimed in claim 135, wherein the first and second layers are coupled to respective first and second body portions of an enclosure at least partially enclosing the layers of electrical connections, the first and second body portions movable to open and close the enclosure.

140. The jackbox as claimed in claim 135, wherein at least the electrical leads of the first and second layers of electrical connections are nested together.

141. The jackbox as claimed in claim 135, wherein the electrical leads and the electrical connectors of the first and second layers of electrical connections are nested together.

142. The jackbox as claimed in claim 135, further comprising a third plurality of electrical connectors to which a third set of electrical leads are releasably connectable to define a third layer of electrical connections, the third layer of electrical connections nested at least partially in the second layer of electrical connections.

143. The jackbox as claimed in claim 135, further comprising a third plurality of electrical connectors to which a third set of electrical leads are releasably connectable to define a third layer of electrical connections, the third layer of electrical connections nested at least partially in and between the first and second layers of electrical connections.

144. The jackbox as claimed in claim 135, wherein the second plurality of electrical connectors are located adjacent to the first plurality of electrical leads and wherein the electrical leads have enlarged ends releasably connectable to the electrical connectors, the second plurality of electrical connectors positioned to block removal of the enlarged ends of the first set of electrical leads.

145. The jackbox as claimed in claim 135, wherein the electrical leads have enlarged ends releasably connectable to the electrical connectors, the enlarged ends of the first and second sets of electrical leads located adjacent to one another, the enlarged ends of the second set of electrical leads positioned to block removal of the enlarged ends of the first set of electrical leads.

146. The jackbox as claimed in claim 135, further comprising an enclosure within which the electrical connectors and electrical leads are located, the enclosure having:
   an open position;
   a closed position;
   an interior area; and
   at least one lead aperture defined therein extending from the interior area to a location outside of the enclosure and through which the electrical leads extend, the first and second layers of electrical connections oriented toward the aperture at least when the enclosure is in its open position.

147. The jackbox as claimed in claim 146, wherein the first and second layers lie substantially in respective first and second substantially parallel planes extending substantially toward the aperture when the enclosure is in its closed position.

148. The jackbox as claimed in claim 146, wherein the first and second layers lie substantially in respective first and second planes converging in a direction toward the aperture when the enclosure is in its closed position.

149. The jackbox as claimed in claim 135, further comprising first and second circuit elements running along and in electrical communication with the electrical connectors in the first and second layers of electrical connections, respectively.

150. The jackbox as claimed in claim 149, wherein the first and second circuit elements are flex circuits.

151. A method of coupling a plurality of electrical leads to a jackbox, the leads carrying signals corresponding to at least one physiological parameter of a patient, the method comprising the steps of:
   opening the jackbox to expose a first and a second plurality of electrical connectors mounted therein;
   connecting the plurality of electrical leads carrying the signals to the first and second pluralities of electrical connectors to create first and second pluralities of electrical connections, respectively;
   closing the jackbox; and
   nesting the first plurality of electrical connections at least partially within the second plurality of electrical connections during the step of closing the jackbox.

152. The method as claimed in claim 151, wherein the nesting step includes at least partially overlapping the first plurality of electrical connections with respect to the second plurality of electrical connections.

153. The method as claimed in claim 151, wherein the first plurality of electrical connections is substantially parallel to the second plurality of electrical connections at least when the jackbox is closed.

154. The method as claimed in claim 151, wherein in the connecting step, enlarged ends of first and second sets of electrical leads are coupled to the first and second pluralities of electrical connectors, and wherein the nesting step includes positioning the enlarged ends of the first set of electrical leads adjacent to the second set of electrical connectors, the enlarged ends of the first set of electrical leads being at least partially blocked from disconnection by the second set of electrical connectors.

155. The method as claimed in claim 151, wherein in the connecting step, enlarged ends of first and second sets of electrical leads are coupled to the first and second pluralities of electrical connectors, and wherein the nesting step includes positioning the enlarged ends of the first set of electrical leads adjacent to the enlarged ends of the second set of electrical leads, the enlarged ends of the first set of electrical leads being at least partially blocked from disconnection by the enlarged ends of the second set of electrical leads.

156. The method as claimed in claim 151, further comprising the step of pivoting at least one of the pluralities of electrical connections during the closing step to orient the electrical connections for nesting.

157. The method as claimed in claim 151, wherein the jackbox includes first and second body parts at least partially enclosing the plurality of electrical connections and movable with respect to one another to open and close the jackbox, the first and second pluralities of electrical connectors coupled to the first and second body parts, respectively, and wherein the opening and closing steps include moving the first and second body parts with respect to one another to move the first and second pluralities of electrical connectors with respect to one another.

158. The method as claimed in claim 157, wherein the closing step includes moving the first and second pluralities of connections together and wherein the opening step includes moving the first and second pluralities of connections apart, the first and second pluralities of connections at least partially overlapping one another when the jackbox is closed.

159. The method as claimed in claim 157, wherein in the connecting step, enlarged ends of first and second sets of electrical leads are coupled to the first and second pluralities of electrical connectors, and wherein the nesting step includes positioning the enlarged ends of the first set of electrical leads adjacent to the second set of electrical connectors, the enlarged ends of the first set of electrical leads being at least partially blocked from disconnection by the second set of electrical connectors.

160. The method as claimed in claim 157, wherein in the connecting step, enlarged ends of first and second sets of electrical leads are coupled to the first and second pluralities of electrical connectors, and wherein the nesting step includes positioning the enlarged ends of the first set of electrical leads adjacent to the enlarged ends of the second set of electrical leads, the enlarged ends of the first set of electrical leads being at least partially blocked from disconnection by the enlarged ends of the second set of electrical leads.

161. The method as claimed in claim 157, wherein the nesting step includes moving the first plurality of electrical connections into a substantially parallel relationship with the second plurality of electrical connections.

162. The method as claimed in claim 157, wherein the nesting step includes moving the first plurality of electrical connections into an angled relationship with the second plurality of electrical connections.

163. The method as claimed in claim 151, wherein the jackbox has a third plurality of electrical connectors to which are connected electrical leads during the connecting step to define a third plurality of electrical connections, and wherein the nesting step includes nesting the third plurality of electrical connections at least partially within at least one of the first and second plurality of electrical connections.

164. The method as claimed in claim 163, wherein at least the plurality of electrical leads connected of the third plurality of electrical connections is nested within at least one of the first and second pluralities of electrical connections.

165. A method of coupling a plurality of electrical leads carrying signals corresponding to at least one physiological parameter of a patient to associated equipment, the method comprising the steps of:
provide a jackbox having at least one electrical connector, the at least one electrical connector having a first orientation in the jackbox;
bending at least a portion of the jackbox to change the orientation of the at least one electrical connector, the portion being comprised of a resilient and deformable material;
connecting an electrical lead to the at least one electrical connector to establish an electrical connection; and
permitting the jackbox to return to a pre-bent form in which the at least one electrical connector is in its first orientation.

166. The method as claimed in claim 165, further comprising the step of opening an enclosure of the jackbox.

167. A jackbox for releasably coupling a plurality of electrical leads to associated equipment, the leads carrying signals corresponding to at least one physiological parameter of a patient, the jackbox comprising:
an enclosure having an open position and a closed position;
a plurality of electrical connectors connectable to at least some of the plurality of electrical leads carrying the signals corresponding to the at least one physiological parameter of the patient, the plurality of electrical connectors located inside the enclosure and accessible when the enclosure is in its open position and substantially inaccessible when the enclosure is in its closed position; and
an amplifier located at least partially within the enclosure and coupled to the plurality of electrical connectors for receiving and amplifying the signals corresponding to the at least one physiological parameter of the patient received from the plurality of electrical connectors.

168. The jackbox as claimed in claim 167, wherein the enclosure comprises resilient deformable material.

169. The jackbox as claimed in claim 167, wherein the jackbox has a first body portion and a second body portion coupled thereto, the first and second body portions movable relative to one another to open and close the jackbox.

170. The jackbox as claimed in claim 167, further comprising a wireless transmitter coupled to the amplifier for transmitting signals received from the plurality of electrical connectors.

171. A jackbox for releasably coupling a plurality of electrical leads to associated equipment, the leads carrying signals corresponding to at least one physiological parameter of a patient, the jackbox comprising:
an enclosure having an open position and a closed position a plurality of electrical connectors connectable to at least some of the plurality of electrical leads carrying the signals corresponding to the at least one physiological parameter of the patient, the plurality of electrical connectors located inside the enclosure and accessible when the enclosure is in its open position and substantially inaccessible when the enclosure is in its closed position; and a wireless transmitter coupled to the plurality of electrical connectors for transmitting the signals corresponding to the at least one physiological parameter of the patient received from the plurality of electrical connectors.

172. The jackbox as claimed in claim 171 further comprising an amplifier coupled to the plurality of electrical connectors for amplifying the signals received from the plurality of electrical connectors.

173. The jackbox as claimed in claim 171, further comprising a digitizer coupled to the plurality of electrical connectors for converting analog signals from the electrical connectors into digital signals.

174. The jackbox as claimed in claim 173, further comprising an amplifier coupled to the digitizer.

175. The jackbox as claimed in claim 1, wherein at least one of the plurality of electrical connectors has a signal conductor and a ground conductor.

176. The jackbox as claimed in claim 175, wherein at least one of the plurality of electrical leads is a two-conductor lead.

177. The jackbox as claimed in claim 1, wherein at least one of the plurality of electrical connectors is a reference connector for releasable connection to at least one of the plurality of electrical leads defining a reference lead.

178. The jackbox as claimed in claim 177, wherein four electrical connectors are reference connectors for releasable connection of up to four reference leads.

179. The method as claimed in claim 22, wherein at least one of the plurality of electrical connectors is a reference connector, the method further comprising releasably connecting reference leads to at least one of the reference connectors prior to closing the enclosure.

180. The method as claimed in claim 22, wherein at least one of the plurality of electrical connectors is a two-conductor connector having a ground conductor and a signal conductor.

181. The method as claimed in claim 180, wherein at least one of the plurality of electrical leads is a two-conductor lead for releasable connection to a two-conductor connector.

* * * * *